United States Patent
Shin et al.

(10) Patent No.: US 9,902,758 B2
(45) Date of Patent: Feb. 27, 2018

(54) THREE-HELIX BUNDLE PROTEIN AND USE THEREOF

(71) Applicant: Samsung Electronics Co., Ltd., Suwon-si, Gyeonggi-do (KR)

(72) Inventors: Dongkyu Shin, Suwon-si (KR); Jung Min Kim, Seoul (KR); Kyoung Hu Lee, Hwaseong-si (KR); Jae Il Lee, Yongin-si (KR); Jung Wook Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/137,942

(22) Filed: Apr. 25, 2016

(65) Prior Publication Data

US 2016/0311878 A1 Oct. 27, 2016

(30) Foreign Application Priority Data

Apr. 23, 2015 (KR) ........................ 10-2015-0057295

(51) Int. Cl.
*A61K 38/00* (2006.01)
*A61P 35/00* (2006.01)
*C07K 14/47* (2006.01)

(52) U.S. Cl.
CPC .......... *C07K 14/4746* (2013.01); *C07K 14/47* (2013.01); *C07K 14/4702* (2013.01); *A61K 38/00* (2013.01); *C07K 2319/00* (2013.01)

(58) Field of Classification Search
CPC ............................ C07K 14/47; C07K 14/4702; C07K 14/4746; C07K 2319/00; A61K 38/00
See application file for complete search history.

(56) References Cited

U.S. PATENT DOCUMENTS

| | | |
|---|---|---|
| 8,163,789 B2 | 4/2012 | Doemling |
| 8,343,760 B2 | 1/2013 | Lu et al. |
| 2012/0328692 A1 | 12/2012 | Lu et al. |
| 2013/0217634 A1 | 8/2013 | Moretti et al. |
| 2014/0018302 A1 | 1/2014 | Walensky et al. |
| 2014/0148443 A1 | 5/2014 | Chu et al. |

FOREIGN PATENT DOCUMENTS

| | | |
|---|---|---|
| JP | 2010-105992 A | 5/2010 |
| JP | 2014-502152 A | 1/2014 |
| WO | WO 2008/106507 A2 | 9/2008 |
| WO | WO 2013/162760 A2 | 10/2013 |
| WO | WO 2014/055039 A1 | 4/2014 |

OTHER PUBLICATIONS

A Comparison of Three- and Four-Helix Bundle TASP Molecules. J Pep Sci, 2002. vol. 8, pp. 275-282.*
Brown et. al., Awakening guardian angels:drugging the p53 pathway, *Nature Reviews—Cancer*, 9:862-873 (2009).
Wade et. al., MDM2, MDMX and p53 in oncogenesis and cancer therapy, *Nature Reviews—Cancer*, 13: 83-96 (2013).

* cited by examiner

*Primary Examiner* — Marcela M Cordero Garcia
(74) *Attorney, Agent, or Firm* — Leydig, Voit & Mayer, Ltd.

(57) ABSTRACT

A three-helix bundle protein, a polynucleotide encoding the three-helix bundle protein, a method of preparing the three-helix bundle protein, and a method of treating a cancer using the three-helix bundle protein.

18 Claims, 8 Drawing Sheets

| heptad position |  |  | a | b | c | d | e | f | g | a | b | c | d | e | f | g | a | b | c | d |  |  |  |  |
|---|---|---|---|---|---|---|---|---|---|---|---|---|---|---|---|---|---|---|---|---|---|---|---|---|
| residue number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| α3D | M | G | S | W | A | E | F | K | Q | R | L | A | A | I | K | T | R | L | Q | A | L | G | G | S |

| heptad position | e | f | g | a | b | c | d | e | f | g | a | b | c | d | e | f | g | a | b | c | d |  |  |  |
|---|---|---|---|---|---|---|---|---|---|---|---|---|---|---|---|---|---|---|---|---|---|---|---|---|
| residue number | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 |
| α3D | E | A | E | L | A | A | F | E | K | E | I | A | A | F | E | S | E | L | Q | A | Y | K | G | K | G |

| heptad position | e | f | g | a | b | c | d | e | f | g | a | b | c | d | e | f | g | a | b | c | d | e | f | g |
|---|---|---|---|---|---|---|---|---|---|---|---|---|---|---|---|---|---|---|---|---|---|---|---|---|
| residue number | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 |
| α3D | N | P | E | V | E | A | L | R | K | E | A | A | I | R | D | E | L | Q | A | Y | R | H | N | - |

FIG. 9A

Three-helix bundle domains and proteins.

| Protein | Species | Function | PDB code |
|---|---|---|---|
| Lysin | *Haliotis rufescens* | Red abalone sperm protein involved in egg penetration | 1lis, 1lyn |
| Enzyme IIA^lactose | *Lactococcus lactis* | Phosphotransferase | 1e2a |
| Protein A (domain B) | *Staphylococcus aureus* | Immunoglobulin-binding protein | 1bdd, 1bdc, 1fc2 |
| Protein A (domain E) | *Staphylococcus aureus* | Immunoglobulin-binding protein | 1edk, 1edi |
| Protein A (domain Z) mutant sequence | *Staphylococcus aureus* | Immunoglobulin-binding protein | 1spz |
| Spectrin (repeat unit) | *Drosophila melanogaster* | Forms protein matrix via actin association | 2spc |
| Er-1, Er-2, Er-10, Er-11 | *Euplotes raikovi* | Rotozoan pheromone proteins | 2erl, 1erc, 1erd, 1erp, 1ery |
| Barstar | *Bacillus amyloliquefaciens* | Barnase-inhibitor protein | 1bta |
| Acyl-CoA binding protein | *Bos taurus* | Ligand-binding protein | 2abd, 1aca |
| Thyroid transcription factor 1 homeodomain | *Rattus rattus* | DNA-binding three-helix bundle | 1ttt |
| Antennapedia homeodomain | *Drosophila melanogaster* | DNA-binding three-helix bundle | 1hom, 2hoa, 1ahd, 1san |
| Oct-1 and Oct-2 POU (homeodomain) | *Homo sapiens* | DNA-binding three-helix bundle | 1oct, 1pof, 1hdp |
| Oct-3 POU (homeodomain) | *Mus musculus* | DNA-binding three-helix bundle | 1oep |
| Engrailed homeodomain protein | *Drosophila melanogaster* | DNA-binding three-helix bundle | 1enh, 1hdd |
| Paired domain protein | *Drosophila melanogaster* | DNA-binding three-helix bundle | 1pdn |
| Paired protein (homeodomain) | *Drosophila melanogaster* | DNA-binding three-helix bundle | 1fjl |
| Fushi Tarazu protein (homeodomain) | *Drosophila melanogaster* | DNA-binding three-helix bundle | 1ftz |
| Transcription factor LFB1 | *Rattus rattus* | DNA-binding three-helix bundle | 1lfb |
| Fli-1 | *Homo sapiens* | DNA-binding three-helix bundle | 1fli |
| Mat A1/alpha 2 (homeodomain) | *Saccharomyces cerevisiae* | DNA-binding three-helix bundle | 1ym, 1apl |

FIG. 9B

Three-helix bundle domains and proteins.

| Protein | Species | Function | PDB code |
|---|---|---|---|
| VND/NK-2 protein (homeodomain) | Drosophila melanogaster | DNA-binding three-helix bundle | 1vnd |
| Heat-shock transcription factor | Kluyveromyces lactis | DNA-binding three-helix bundle | 2hts, 3hsf |
| Heat-shock transcription factor | Drosophila melanogaster | DNA-binding three-helix bundle | 1hks, 1hkt |
| Transcription factor PU.1 (ets domain) | Mus musculus | DNA-binding three-helix bundle | 1pue |
| ETS-1 transcription factor (ets domain) | Mus musculus | DNA-binding three-helix bundle | 1etc, 1etd |
| Histone H1 | Gallus gallus | DNA-binding three-helix bundle | 1ghc |
| Histone H5 | Gallus gallus | DNA-binding three-helix bundle | 1hst |
| CAP C-terminal domain | Escherichia coli | DNA-binding three-helix bundle | 1cgp, 1ber, 3gap |
| LexA repressor (DNA-binding domain) | Escherichia coli | DNA-binding three-helix bundle | 1lea, 1leb |
| c-Myb (DNA-binding domain) | Mus musculus | DNA-binding three-helix bundle | 1mbe, 1mbl, 1mbg, 1mbh, 1mbj, 1mbk, 1mse, 1msf |
| Biotin repressor (N-terminal domain) | Escherichia coli | DNA-binding three-helix bundle | 1bia, 1bib |
| Rap1 (DNA-binding domain) | Saccharomyces cerevisiae | DNA-binding three-helix bundle | 1ign |
| Gamma/delta resolvase (C-terminal domain) | Escherichia coli | DNA-binding three-helix bundle | 1res, 1ret, 1gdt |
| Hin recombinase (DNA-binding domain) | Salmonella | DNA-binding three-helix bundle | 1hcr |
| Iron-dependent repressor protein | Corynebacterium diphtheriae | DNA-binding three-helix bundle | 1dpr, 1tdx |

US 9,902,758 B2

THREE-HELIX BUNDLE PROTEIN AND USE THEREOF

CROSS-REFERENCE TO RELATED APPLICATIONS

This application claims the benefit of Korean Patent Application No. 10-2015-0057295 filed on Apr. 23, 2015 in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 16,839 Byte ASCII (Text) file named "723490_ST25.TXT," created on Apr. 8, 2016.

BACKGROUND OF THE INVENTION

1. Field

Provided is a three-helix bundle protein, a polynucleotide encoding the three-helix bundle protein, a method of preparing the three-helix bundle protein, an agent for inhibiting HDM2 and/or HDMX including the three-helix bundle protein as an active ingredient, and a pharmaceutical composition for preventing and/or treating a cancer including the three-helix bundle protein as an active ingredient.

2. Description of the Related Art

HDM2 and/or HDMX (or HDM4), are negative regulators of the tumor suppressor p53, and act by stimulating p53 ubiquitination, thereby leading to the degradation of p53 by the proteosome in a cell. HDM2 and/or HDMX are reported to be over-expressed in various kinds of cancers and interact with p53 by recognizing and binding to the transcription activation domain (TAD) positioned at the N-terminus of p53 through direct protein-protein interaction (PPI). Therefore, the development of antagonists capable of inhibiting the PPI in order to prevent intracellular p53 degradation may provide new cancer therapeutics. One such PPI antagonist, Nutlin-3, has been shown to inhibit only the binding of HDM2 and p53, and has a high level of cytotoxicity.

Therefore, there is a need to develop new compounds capable of effectively inhibiting degradation of p53 by HDM2 and/or HDMX that have low cytotoxicity. This invention provides such compounds.

BRIEF SUMMARY OF THE INVENTION

One embodiment of the invention provides a three-helix bundle protein. The three-helix bundle protein mimics a binding domain of p53 that interacts (binds) with HDM2 and/or HDMX, thereby possessing high binding affinity to HDM2 and/or HDMXA.

Another embodiment provides a polynucleotide encoding the three-helix bundle protein.

Another embodiment provides an inhibitor of HDM2 and/or HDM, including the three-helix bundle protein as an active ingredient.

Another embodiment provides a pharmaceutical composition for preventing and/or treating a cancer, including the three-helix bundle protein as an active ingredient.

Another embodiment provides a method of preparing a three-helix bundle protein having a high affinity to HDM2 and/or HDMX.

BRIEF DESCRIPTION OF THE DRAWINGS

FIG. 9A and FIG. 9B provide examples of natural three-helix bundle proteins.

DETAILED DESCRIPTION OF THE INVENTION

In this description, small protein antagonists having an increased affinity to HDM2/HDMX in a cell compared to wild-type (WT) p53 were developed. The small protein antagonists are obtained by protein grafting technology using a three-helix bundle protein as a template. The small protein antagonists are designed to have rapid folding while possessing similar properties to stable natural proteins. Therefore, novel HDM2/HDMX dual inhibitors with high affinity to HDM2/HDMX can be obtained, while maintaining the structural advantages of the three-helix bundle protein.

One embodiment of the invention provides a novel three-helix bundle protein. The three-helix bundle protein may be a p53 mimetic molecule, with a high affinity for HDM2 and/or HDMX, that maintains the structural advantages of preexisting three-helix bundle proteins, and mimics the HDM2 and/or HDMX binding site on p53. Therefore, the three-helix bundle protein competes with p53 for binding to HDM2 and/or HDMX, thereby inhibiting the binding between p53 and HDM2 and/or HDMX, Thus, the three-helix bundle of one embodiment of the invention effectively inhibits p53 biding ability and/or p53 degradation ability of HDM2 and/or HDMX.

Figure 1:
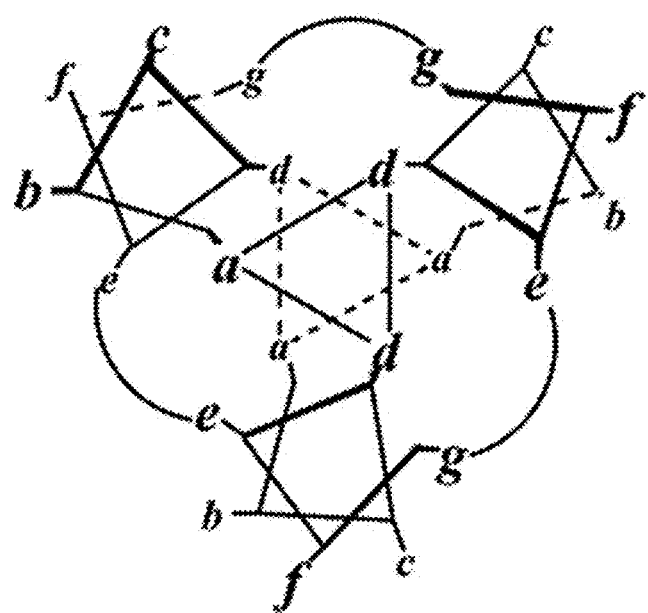
FIG. 1 is a schematic that shows the transsection of the three-helix bundle of a three-helix bundle protein.

The three-helix bundle protein may be a protein comprising a triple-folded single-stranded structure having three helices and loops linking the helices, or a three-stranded coiled coil structure wherein three helical strands, which are not linked to one another, are overlapped (layered) and coiled. A single helical structure comprised in the three-helix bundle protein comprises at least one heptad (e.g., 1 to about 100, 1 to about 50, 1 to about 20, 1 to about 15, 1 to about 13, about 2 to about 100, about 2 to about 50, about 2 to about 20, about 2 to about 15, about 2 to about 13, about 3 to about 100, about 3 to about 50, about 3 to about 20, about 3 to about 15, about 3 to about 13, about 5 to about 100, about 5 to about 50, about 5 to about 20, about 5 to about 15, about 5 to about 13 heptads) and each heptad comprises 7 amino acid residues. The positions of the 7 amino acid residues are indicated as a, b, c, d, e, f, and g in FIG. 1, respectively. The starting point (the first amino acid residue) and the end point (the last amino acid residue) of each heptad in each helix may be independently selected from the positions a, b, c, d, e, f, and g; e.g., the starting point and end point may be positioned 6 residues away from each other (not counting the starting and end points). In addition, each helix may further comprise at least one peptide (e.g., 1 to about 10, 1 to about 8, 1 to about 6, 1 to about 5, 1 to about 4, or 1 or about 3 peptides) at an N-terminus, a C-terminus, or both termini (in this case, 2 or more peptide structures are comprised), or inside (e.g., inside of at least one heptad repeated and/or between a heptad and adjacent heptad as a linker linking the heptads) of the helix, wherein the peptide may have a linear structure or a beta-sheet structure in length of 1 to about 100 aa (amino acid), 1 to about 50 aa, 1 to about 20 aa, 1 to about 15 aa, 1 to about 10 aa, or 1 to about 5 aa.

The three-helix bundle protein may be selected from the group consisting of natural three-helix bundle proteins modified as described herein, and artificial (designed) three-helix bundle proteins which are designed so as to have the three-helix bundle protein structure as described above. Examples of natural three-helix bundle proteins are illustrated in FIGS. 9A and 9B.

In addition, the artificial three-helix bundle protein may be selected from any protein designed so as to have a three-helix bundle protein structure, and may be at least one selected from the group consisting of synthetic or recombinant versions of the three-helix bundle proteins illustrated in Table 1 and alpha3D (a3d; SEQ ID NO: 6), but not be limited thereto.

The primary, secondary, tertiary, and/or quaternary structures of the three-helix bundle protein and p53 protein are compared (matched) to each other, to determine (i) a region of the three-helix bundle protein corresponding to a N-terminal region of the transactivation domain (TAD) of p53, which is a binding site of p53 with HDM2 and/or HDMX, wherein the N-terminal region of the TAD may comprise "QETFSDLWKLLPENNVLS" (SEQ ID NO: 2) or "ETFSDLWKLLPEN" (SEQ ID NO: 3); and/or (ii) at least one position in the corresponding region of the three-helix bundle protein, the position corresponding to at least one critical residue of the N-terminal region of the TAD of p53 in binding to HDM2 and/or HDMX, and wherein the critical residue of the N-terminal region of the TAD of p53 may at least one selected from the group consisting of phenylalanine (F) (the $5^{th}$ amino acid residue of SEQ ID NO: 2 or the $3^{rd}$ amino acid residue of SEQ ID NO: 3), tryptophan (W) (the $9^{th}$ amino acid residue of SEQ ID NO: 2 or the $7^{th}$ amino acid residue of SEQ ID NO: 3), and leucine (L) (the $12^{th}$ amino acid residue of SEQ ID NO: 2 or the $10^{th}$ amino acid residue of SEQ ID NO: 3).

At least one amino acid of the above-determined corresponding positions of the three-helix bundle protein may be substituted with a different amino acid, which is an amino acid residue at the corresponding position in the N-terminal region of the TAD of p53, i.e., amino acid F, W and/or L, to provide a modified three-helix bundle protein having improved binding affinity to HDM2 and/or HDMX.

The positions of the three-helix bundle protein (to be substituted thereby producing a modified three-helix bundle protein) corresponding to the critical residues of the N-terminal region of the TAD of p53, i.e., F, W, and L indicated in SEQ ID NO: 2 and/or SEQ ID NO: 3 above, may be at least one combination (b-f-b' and/or 'f-c-f') selected from $b''$-$f''$-$b''^{n+1}$ and $f'''$-$c^{m+1}$-$f'''^{m+1}$ in heptad(s) of the three-helix bundle protein, in order.

For example, the positions in the three-helix bundle protein corresponding to the critical residues of the N-terminal region of the TAD of p53 (i.e., F, W, and L indicated in SEQ ID NO: 2 and/or SEQ ID NO: 3) may be (i) positions 'b' or $'b''$' (corresponding to 'F' of SEQ ID NO: 2 and/or SEQ ID NO: 3) and 'f' or $'f''$' (corresponding to 'W' of SEQ ID NO: 2 and/or SEQ ID NO: 3) in a first heptad (that can be randomly selected in the three-helix bundle protein) and position 'b' or $'b''^{n+1}$' (corresponding to 'L' of SEQ ID NO: 2 and/or SEQ ID NO: 3) in a second heptad that is adjacent to the C-terminus of the first heptad (relating to the combination 'b-f-b' or $'b''$-$f''$-$b''^{n+1}$'); and/or (ii) position 'f' or $'f''$' (corresponding to 'F' of SEQ ID NO: 2 and/or SEQ ID NO: 3) in a first heptad (that can be randomly selected in the three-helix bundle protein), and positions 'c' or $'c''^{n+1}$' (that can be randomly selected in the three-helix bundle protein) and 'f' or $'f''^{n+1}$' (corresponding to 'L' of SEQ ID NO: 2 and/or SEQ ID NO: 3) in a second heptad that is adjacent to the C-terminus of the first heptad (relating to the combination 'f-c-f' or $'f'''$-$c^{m+1}$-$f'''^{m+1}$').

The 'n' and 'm' independently refer to the numbering of the consecutive repeated heptad numbers in order from N-terminus to C-terminus, and may be the same or different from each other. For example, the term $'b^1$' refers to the position 'b' of the first heptad from the N-terminus of the three-helix bundle protein, and the term $'b^2$' refers to the position 'b' of the second heptad from the N-terminus of the three-helix bundle protein. The 'n' and 'm' may be at least one integer independently selected from the repeat number of heptads comprised in the three-helix bundle protein. The 'n' may be an integer or at least two non-consecutive integers selected from 1 to 100, 1 to 50, 1 to 20, 1 to 15, 1 to 13, 1 to 10, or 1 to 5, for example, one integer or two or three non-consecutive integers selected from 1, 2, 3, 4, and 5, or one integer or two non-consecutive integers selected from 1, 2, and 5. The 'm' may be an integer or at least two non-consecutive integers selected from 1 to 100, 1 to 50, 1 to 20, 1 to 15, 1 to 13, 1 to 10, 3 to 100, 3 to 50, 3 to 20, 3 to 15, 3 to 13, 3 to 10, 5 to 100, 5 to 50, 5 to 20, 5 to 15, 5 to 13, or 5 to 10, for example, one integer or two or three non-consecutive integers selected from 6, 7, 8, 9, and 10, or one integer or two non-consecutive integers selected from 7, 8, and 9. In an embodiment, the 'n' may be less than the 'm', which means that the combination $'b''$-$f''$-$b''^{n+1}$' may be positioned more closely to N-terminal side than the combination $'f'''$-$c^{m+1}$-$f_{m+1}$', in the three-helix bundle protein.

For example, the positions in three-helix bundle protein corresponding to the critical residues of the N-terminal region of TAD of p53 protein in binding to HDM2 and/or HDMX may be at least one combination selected from the group consisting of $b^1$-$f^1$-$b^2$, $b^2$-$f^2$-$b^3$, $b^3$-$f^3$-$b^4$, $b^4$-$f^4$-$b^5$, $b^5$-$f^5$-$b^6$, $f^6$-$c^7$-$f^7$, $f^7$-$c^8$-$f^8$, $f^8$-$c^9$-$f^9$, and $f^9$-$c^{10}$-$f^{10}$, or at least one combination selected from the group consisting of $b^1$-$f^1$-$b^2$, $b^2$-$f^2$-$b^3$, $b^5$-$f^5$-$b^6$, $f^8$-$c^9$-$f^9$, and $f^9$-$c^{10}$-$f^{10}$. Therefore, the three-helix bundle protein may be modified by substituting the amino acid residues at the positions corresponding to the critical residues of the N-terminal region of TAD of p53 protein with F(phenylalanine), W(tryptophan), and L(leucine) in b-f-b and/or f-c-f order (for example, in case of the combination $'b''$-$f''$-$b''^{n+1}$', the amino acid at the position $'b''$' is substituted with F, the amino acid at the position $'f''$' with W, and the amino acid at the position $'b''^{n+1}$' with L; and in case of the combination $'f'''$-$c^{m+1}$-$f'''^{m+1}$', the amino acid at the position $'f'''$' is substituted with F, the amino acid at the position '$c^{m+1}$' with W, and the amino acid at the position '$f^{m+1}$' with L), thereby having a similar structure to that of the N-terminal region of TAD of p53 protein, and thus, being capable of exhibiting an binding ability to HDM2 and/or HDMX.

Therefore, the modified three-helix bundle protein may be one wherein amino acid residues of at least one combination selected from the group consisting of '$b''$-$f''$-$b''^{+1}$' and '$f'''$-$c^{m+1}$-$f^{m+1}$' in a three-helix bundle protein ('b-f-b' and/or 'f-c-f'; for example, one or two combinations selected from the group consisting of '$b''$-$f''$-$b''^{+1}$' (combination 1), one or two combinations selected from the group consisting of '$f'''$-$c^{m+1}$-$f^{m+1}$' (combination 2), or a combination of combination 1 and combination 2) are substituted with F(phenylalanine), W(tryptophan), and L(leucine), respectively, in $b''$-$f''$-$b''^{+1}$ and/or $f'''$-$c^{m+1}$-$f^{m+1}$ order. In case two or more combinations are substituted, the combinations may be selected so that the positions 'b' or 'f' do not overlap with each other. The 'n' and 'm' are as described above.

In an embodiment, the modified three-helix bundle protein may be one wherein amino acid residues of at least one combination selected from the group consisting of $b^1$-$f^1$-$b^2$, $b^2$-$b^2$-$b^3$, $b^3$-$f^3$-$b^4$, $b^4$-$f^4$-$b^5$, $b^5$-$f^5$-$b^6$, $f^6$-$c^7$-$f^7$, $f^7$-$c^8$-$f^8$, $f^8$-$c^9$-$f^9$, and $f^9$-$c^{10}$-$f^{10}$, for example, $b^1$-$f^1$-$b^2$, $b^2$-$f^2$-$b^3$, $b^3$-$f^3$-$b^4$, $b^4$-$f^4$-$b^5$, $b^5$-$f^5$-$b^6$, $f^6$-$c^7$-$f^7$, $f^7$-$c^8$-$f^8$, $f^8$-$c^9$-$f^9$, and $f^9$-$c^{10}$-$f^{10}$, in a three-helix bundle protein, are substituted with F(phenylalanine), W(tryptophan), and L(leucine), respectively, in $b''$-$f''$-$b''^{+1}$ and/or $f'''$-$c^{m+1}$-$f^{m+1}$ order (in case two or more combinations are substituted, the combinations may be selected so that the positions 'b' or 'f' do not overlap with each other). For example, the modified three-helix bundle protein may be one wherein amino acid residues of a combination (combination 1) of $b^1$-$f^1$-$b^2$, $b^2$-$f^2$-$b^3$, $b^3$-$f^3$-$b^4$, $b^4$-$f^4$-$b^5$, or $b^5$-$f^5$-$b^6$, a combination (combination 2) of $f^6$-$c^7$-$f^7$, $f^7$-$c^8$-$f^8$, $f^8$-$c^9$-$f^9$, or $f^9$-$c^{10}$-$f^{10}$, or a combination of the combination 1 and the combination 2, in a three-helix bundle protein (e.g., a combination (combination 1') of $b^1$-$f^1$-$b^2$, $b^2$-$f^2$-$b^3$, or $b^5$-$f^5$-$b^6$, a combination (combination 2') of $f^8$-$c^9$-$f^9$ or $f^9$-$c^{10}$-$f^{10}$, or both of the combination 1 and the combination 2) are substituted with F(phenylalanine), W(tryptophan), and L(leucine), respectively, in $b''$-$f''$-$b''^{+1}$ and/or $f'''$-$c^{m+1}$-$f^{m+1}$ order.

In particular, the modified three-helix bundle protein may comprise at least one substitution selected from the group consisting of:

(1) a substitution of at least one selected from amino acid residues of a three-helix bundle protein, which are at the positions corresponding to amino acid residue 'F(phenylalanine)' at the $5^{th}$ position of SEQ ID NO: 2 or the $3^{rd}$ position of SEQ ID NO: 3 (e.g., the amino acid residues of a three-helix bundle protein may be at the position $b''$ and/or fin as described above), with F(phenylalanine), H (histidine), or Y (tyrosine), for example, F, wherein the number of the amino acid residues corresponding to 'F' of SEQ ID NO: 2 or 3 present in the three-helix bundle protein may be one or at least two (e.g., 2 to 5 or 2 to 3) per a helix;

(2) a substitution of at least one selected from amino acid residues of a three-helix bundle protein, which are at the positions corresponding to amino acid residue 'W(tryptophan)' at the $9^{th}$ position of SEQ ID NO: 2 or the $7^{th}$ position of SEQ ID NO: 3 (e.g., the amino acid residues of a three-helix bundle protein may be at the position $f''$ and/or $c^{m+1}$ as described above), with W(tryptophan), wherein the number of the amino acid residues corresponding to 'F' of SEQ ID NO: 2 or 3 present in the three-helix bundle protein may be one or at least two (e.g., 2 to 5 or 2 to 3) per a helix; and (3) a substitution of at least one selected from amino acid residues of a three-helix bundle protein, which are at the positions corresponding to amino acid residue 'L(leucine)' at the $12^{th}$ position of SEQ ID NO: 2 or the $10^{th}$ position of SEQ ID NO: 3 (e.g., the amino acid residues of a three-helix bundle protein may be at the position $b''^{+1}$ and/or $f^{m+1}$ as described above), with L(leucine), wherein the number of the amino acid residues corresponding to 'L' of SEQ ID NO: 2 or 3 present in the three-helix bundle protein may be one or at least two (e.g., 2 to 5 or 2 to 3) per a helix.

That is, the modified three-helix bundle protein may be a three-helix bundle protein, wherein:

a) at least one position of a three-helix bundle protein is phenylalanine, wherein the at least one position corresponds to the $5^{th}$ position of SEQ ID NO: 2 or the $3^{rd}$ position of SEQ ID NO: 3;

b) at least one position of a three-helix bundle protein is tryptophan, wherein the at least one position corresponds to the $9^{th}$ position of SEQ ID NO: 2 or the $7^{th}$ position of SEQ ID NO: 3, c) at least one position of a three-helix bundle protein is leucine, wherein the at least one position corresponds to the $12^{th}$ position of SEQ ID NO: 2 or the $10^{th}$ position of SEQ ID NO: 3, or d) a combination thereof.

For example, in the modified three-helix bundle protein, the positions $b''$, $f''$, and $b''^{+1}$ of a three-helix bundle protein may be phenylalanine, tryptophan, and leucine, in order; and/or the positions $f'''$, $c^{m+1}$, and $f^{m+1}$ of a three-helix bundle protein may be phenylalanine, tryptophan, and leucine, in order.

The positions of a three-helix bundle protein to be modified (substituted) (i.e., the positions corresponding to the amino acid residues F, W, and L present in the N-terminal region (e.g., SEQ ID NO: 2 or SEQ ID NO: 3) of TAD of p53 protein, which are critical in binding with HDM2 and/or HDMX) may be determined through an amino acid sequence alignment and/or a tertiary structure alignment with that of p53 protein by any conventional method. For example, the position to be modified may be at least one selected from the positions b, c, and f in a three-helix bundle protein, and more detailed matters are as described above.

In an embodiment, the modified three-helix bundle protein may comprise at least one amino acid substitution selected from the group consisting of:

(i) a substitution of at least one amino acid selected from the positions 'b' in a three-helix bundle protein (the positions 'b' may be present in a three-helix bundle protein as many as the number of heptads comprised in the three-helix bundle protein) independently with phenylalanine (F) or leucine (L);

(ii) a substitution of at least one amino acid selected from the positions 'c' in a three-helix bundle protein (the positions 'c' may be present in a three-helix bundle protein as many as the number of heptads comprised in the three-helix bundle protein) independently with tryptophan (W); and (iii) a substitution of at least one amino acid selected from the positions 'f' in a three-helix bundle protein (the positions 'f' may be present in a three-helix bundle protein as many as the number of heptads comprised in the three-helix bundle protein) independently with tryptophan (W), phenylalanine (F) or leucine (L).

More detailed matters about the positions b, c, and f in a three-helix bundle protein and an amino acid to be substituted for each position are as described above.

The modified three-helix bundle protein may comprise further amino acid substitution and/or insertion, in addition to the modifications at the positions corresponding to the amino acid residues F, W, and L of N-terminal region of TAD of p53 as described above, so that the modified three-helix bundle protein can avoid a structural conflict with HDM2 and/or HDMX thereby more strongly binding with HDM2 and/or HDMX. In this case, the positions in the modified three-helix bundle protein to be further modified (substituted and/or inserted) may be determined by aligning the modified three-helix bundle protein and a MI and pDIQ complex (PDB code: 3EQS, 3JZS) based on the positions of the modified three-helix bundle protein corresponding to residues F, W, and L of N-terminal region of TAD of p53, and then, searching a position(s) of the modified three-helix bundle protein for removing physical conflict with HDM2 and/or HDMX.

For example, the positions in the modified three-helix bundle protein to be further modified (substituted and/or inserted) for avoiding physical conflict and/or strengthening the binding with HDM2 and/or HDMX may be at least one selected from positions e'. In addition to at least one selected from positions 'e', the modified three-helix bundle protein to be further modified may be at least one selected from positions 'b' other than the positions 'b' in the combination 'b$^n$-f$^n$-b$^{n+1}$' to be substituted with phenylalanine (F) or leucine (L), at least one selected from positions 'c' other than the positions 'c' in the combination 'f$^m$-c$^m$-f$^{m+1}$' to be substituted with tryptophan (W), at least one selected from positions 'g', or a combination thereof. The amino acids to be additionally substituted (i.e., inserted in replacement) for the original amino acids in a three-helix bundle protein may be independently selected from the group consisting of glycine (G), serine (S), alanine (A), glutamic acid (E), tyrosine (Y), tryptophan (W), and the like.

For example, in the additional amino acid substitutions, i) the amino acid substitution at position 'e' may be performed by substituting at least one amino acid at positions 'e' in a three-helix bundle protein independently with glycine (G), serine (S), alanine (A), tyrosine (Y), or tryptophan (W);

ii) the amino acid substitution at position 'b' may be performed by substituting at least one amino acid at positions 'b' in a three-helix bundle protein (wherein the position 'b' is other than the positions 'b' in the combination 'b-f-b' to be substituted with phenylalanine (F) or leucine (L)) independently with tyrosine (Y) or tryptophan (W);

iii) the amino acid substitution at position 'c' may be performed by substituting at least one amino acid at positions 'c' in a three-helix bundle protein (wherein the position 'c' is other than the positions 'c' in the combination 'f-c-f' to be substituted with tryptophan (W)) with glutamic acid (E); and/or iv) the amino acid substitution at positions 'g' may be performed by substituting at least one amino acid at position 'g' in a three-helix bundle protein independently with glycine (G), serine (S), or alanine (A).

v) Optionally, the modified three-helix bundle protein may further comprise one or at least two (e.g., 2-5 or 2-3) additional amino acid residues at C-terminus thereof. In this case, the amino acid to be additionally added (inserted) in the modified three-helix bundle protein may be any amino acid with no limitation; for example, at least one independently selected from the group consisting of proline (P), serine (S), alanine (A), and the like, but not be limited thereto.

That is, in the three-helix bundle protein, i) at least one selected from positions 'e' in a three-helix bundle protein may be independently glycine, serine, alanine, tyrosine, or tryptophan;

ii) at least one selected from positions 'b' in a three-helix bundle protein may be independently tyrosine or tryptophan, wherein the position 'b' is other than the positions 'b' where phenylalanine or leucine is present;

iii) at least one selected from positions 'c' in a three-helix bundle protein may be glutamic acid, wherein the position 'c' is other than the positions 'c' where tryptophan is present;

iv) at least one selected from positions 'g' in a three-helix bundle protein is independently glycine, serine, or alanine; and/or v) 2 to 5 amino acid residues are added to the C-terminus of a three-helix bundle protein.

In one embodiment, the modified three-helix bundle protein may be one modified from alpha3D protein (a3D; SEQ ID NO: 6) as a template. In this case, the modified three-helix bundle protein may be one modified by at least one amino acid substitution selected from the groups consisting of:

1) substitutions of the amino acid at the 5$^{th}$ position of SEQ ID NO: 6 (corresponding to the position 'b' of the first heptad (b$^1$)) with phenylalanine (F), the amino acid at the 9$^{th}$ position of SEQ ID NO: 6 (corresponding to the position 'f' of the first heptad (f$^1$) with tryptophan (W), and/or the amino acid at the 12$^{th}$ position of SEQ ID NO: 6 (corresponding to the position 'b' of the second heptad (b$^2$)) with leucine (L);

2) substitutions of the amino acid at the 12$^{th}$ position of SEQ ID NO: 6 (corresponding to the position 'b' of the second heptad (b$^2$)) with phenylalanine (F), the amino acid at the 16$^{th}$ position of SEQ ID NO: 6 (corresponding to the position 'f' of the second heptad (f$^2$)) with tryptophan (W), and/or the amino acid at the 19$^{th}$ position of SEQ ID NO: 6 (corresponding to the position 'b' of the third heptad (b$^3$)) with leucine (L);

3) substitutions of the amino acid at the 36$^{th}$ position of SEQ ID NO: 6 (corresponding to the position 'b' of the fifth heptad (b$^5$)) with phenylalanine (F), the amino acid at the 40$^{th}$ position of SEQ ID NO: 6 (corresponding to the position 'f' of the fifth heptad (f$^5$)) with tryptophan (W), and/or the amino acid at the 43$^{rd}$ position of SEQ ID NO: 6 (corresponding to the position 'b' of the sixth heptad (b$^6$)) with leucine (L);

4) substitutions of the amino acid at the 58$^{th}$ position of SEQ ID NO: 6 (corresponding to the position 'f' of the seventh heptad (f$^7$)) with phenylalanine (F), the amino acid at the 62$^{nd}$ position of SEQ ID NO: 6 (corresponding to the position 'c' of the eighth heptad (c$^8$)) with tryptophan (W), and/or the amino acid at the 65$^{th}$ position of SEQ ID NO: 6 (corresponding to the position 'f' of the eighth heptad (f$^8$)) with leucine (L);

5) substitutions of the amino acid at the 65$^{th}$ position of SEQ ID NO: 6 (corresponding to the position 'f' of the eighth heptad (e)) with phenylalanine (F), the amino acid at the 69$^{th}$ position of SEQ ID NO: 6 (corresponding to the position 'c' of the ninth heptad (c$^9$)) with tryptophan (W), and/or the amino acid at the 72$^{nd}$ position of SEQ ID NO: 6 (corresponding to the position 'f' of the ninth heptad (f$^9$)) with leucine (L); or a combination of at least two of 1) to 5).

In another embodiment, the modified three-helix bundle protein derived from a3D protein (SEQ ID NO: 6; template) may further comprise additional amino acid modification (substitution and/or insertion) in addition to the amino acid substitutions 1) to 5) as described above, and for example, the additional amino acid modification (substitution and/or insertion) may be at least one selected from the followings:

6) a substitution of the amino acid at the 8$^{th}$ position of SEQ ID NO: 6 (corresponding to the position e' of the first heptad) with serine (S) or alanine (A);

7) a substitution of the amino acid at the 13$^{th}$ position of SEQ ID NO: 6 (corresponding to the position 'c' of the second heptad) with glutamic acid (E);

8) a substitution of the amino acid at the 15$^{th}$ position of SEQ ID NO: 6 (corresponding to the position 'e' of the second heptad) with tyrosine (Y);

9) a substitution of the amino acid at the 39$^{th}$ position of SEQ ID NO: 6 (corresponding to the position e' of the fifth heptad) with tyrosine (Y);

10) a substitution of the amino acid at the 61$^{st}$ position of SEQ ID NO: 6 (corresponding to the position 'b' of the eighth heptad) with tyrosine (Y);

11) a substitution of the amino acid at the 68$^{th}$ position of SEQ ID NO: 6 (corresponding to the position 'b' of the ninth heptad) with tyrosine (Y);

12) a substitution of the amino acid at the 73$^{rd}$ position of SEQ ID NO: 6 (corresponding to the position 'g' of the ninth heptad) with serine (S); and 13) an insertion of proline (P) at the C-terminus of SEQ ID NO: 6 (corresponding to the 74$^{th}$ position of SEQ ID NO: 6).

Alternatively, the modified three-helix bundle protein may be expressed by the following sequences:

(SEQ ID NO: 28)
MGSWX$_1$EFX$_2$X$_3$R LX$_4$X$_5$IX$_6$X$_7$RLX$_8$A LGGSEAELAA

FEKEIX$_9$AFX$_{10}$X$_{11}$ ELX$_{12}$AYKGKGN PEVEALRX$_{13}$EA

X$_{14}$X$_{15}$IRX$_{16}$ELX$_{17}$X$_{18}$Y RX$_{19}$X$_{20}$X$_{21}$ wherein, X$_1$ is A or F; X$_2$ is K, S, or A; X$_3$ is Q or W; X$_4$ is A, F, or L; X$_5$ is A or E; X$_6$ is K or Y; X$_7$ is T or W; X$_8$ is Q or L; X$_9$ is A or F; X$_{10}$ is E or Y; X$_{11}$ is S or W; X$_{12}$ is Q or L; X$_{13}$ is K or F; X$_{14}$ is A or Y; X$_{15}$ is A or W; X$_{16}$ is D, F, or L; X$_{17}$ is Q or Y; X$_{18}$ is A or W; X$_{19}$ is H or L; X$_{20}$ is N or S; and X$_{21}$ is absent or P.

The amino acid sequence of SEQ ID NO: 28 is not the same with that of SEQ ID NO: 6.

In an embodiment, the modified three-helix bundle protein may be comprise or consist essentially of the amino acid sequence selected from the group consisting of SEQ ID NOs: 7, 8, 9, 10, 11, 12, 13, 14, 15, and 16.

The modified three-helix bundle protein may maintain the structure and stability of three-helix bundle proteins, and possess binding ability to HDM2 and/or HDMX. For example, the modified three-helix bundle protein may have HDM2 binding affinity (Kd) of 100 nM or less, 50 nM or less, 30 nM or less, or 20 nM or less, for example, 0.1 to 100 nM, 0.1 to 50 nM, 0.1 to 30 nM, or 0.1 to 20 nM. In addition, the modified three-helix bundle protein may have HDMX binding affinity (Kd) of 200 nM or less, 150 nM or less, 120 nM or less, or 100 nM or less, for example, 0.1 to 200 nM, 0.1 to 150 nM, 0.1 to 120 nM, or 0.1 to 100 nM.

In another embodiment, the modified three-helix bundle protein may further comprise a cell penetrating peptide (CPP). The cell penetrating peptide may be any peptide having cell membrane penetrating activity. The cell penetrating peptide may be at least one selected from the group consisting of:

TAT peptide (RKKRRQRRR; SEQ ID NO: 18),
membrane translocating sequences (MTS; e.g., AAVALLPAVLLALLAP (SEQ ID NO: 19), etc.),
MTS fragments (peptides comprising or consisting essentially of 7 to 16 consecutive amino acids of the MTS; for example, AAVALLP (SEQ ID NO: 20), AVLLALLAP (SEQ ID NO: 21), etc.), and
fusion peptides comprising the MTS or MTS fragment and nuclear localization sequence (NLS; e.g., KKKRK (SEQ ID NO: 22), KKKR (SEQ ID NO: 23), KKKRKR (SEQ ID NO: 24), RRRRR (SEQ ID NO: 25), RRRRRR (SEQ ID NO: 26), etc.), wherein the NLS is coupled to the N-terminus and/or C-terminus of the MTS or MTS fragment, for example, C-terminus: e.g., AAVALLPAVLLALLAPKKKRK(SEQ ID NO: 27), etc.).

The cell penetrating peptide may be coupled (linked) to the modified three-helix bundle protein, for example via a chemical bond (e.g., covalent bond), at the N-terminus and/or C-terminus and/or an amino acid residue capable of forming a chemical bond (e.g., covalent bond). Such coupling of the cell penetrating peptide may lead to improve the efficiency of intracellular delivery of the modified three-helix bundle protein, thereby achieving excellent inhibiting effect against HDM2 and/or HDMX, and/or improved anticancer effect.

HDM2 and HDMX (also called as HDM4) are negative regulators of human tumor suppressor, p53. HDM2 and HDMX function as E3 ubiquitin ligase recognizing N-terminal region of transactivation domain (TAD) and p53 transcription inhibitor. HDM2 may comprise or consist essentially of NP_002383.2 or the amino acid sequence encoded by NM_001145336.1 (cDNA), but not be limited thereto. HDMX may comprise or consist essentially of NP_001191100.1 or the amino acid sequence encoded by NM_001204171.1 (cDNA), but not be limited thereto.

The modified three-helix bundle protein exhibits higher binding ability (binding affinity) with HDM2/HDMX than wild-type p53, and competes with p53 for binding to HDM2/HDMX, thereby inhibiting the activity of HDM2/HDMX to bind and degrade p53. Therefore, the modified three-helix bundle protein can function as a dual inhibitor of HDM2 and HDMX. In addition, the modified three-helix bundle protein can inhibit the activity of HDM2/HDMX to bind and degrade p53 tumor suppressor, thereby activating the tumor suppressing activity of p53. Therefore, the modified three-helix bundle protein can function as an anticancer agent.

Another embodiment provides a pharmaceutical composition comprising a pharmaceutically effective amount of the modified three-helix bundle protein, a polynucleotide encoding the modified three-helix bundle protein, a recombinant vector comprising the polynucleotide, a recombinant cell comprising the polynucleotide or the recombinant vector, or a combination thereof. The pharmaceutical composition may have HDM2/HDMX inhibiting effects and/or anticancer effects.

In particular, an embodiment provides a pharmaceutical composition for inhibiting HDM2 and/or HDMX, comprising the modified three-helix bundle protein as an active ingredient. Another embodiment provides a method of inhibiting HDM2 and/or HDMX, comprising administering a pharmaceutically effective amount of the modified three-helix bundle protein to a subject in need of inhibiting HDM2 and/or HDMX. The method may further comprises a step of identifying (selecting) a subject in need of inhibiting HDM2 and/or HDMX, prior to the step of administering.

Another embodiment provides a pharmaceutical composition for preventing and/or treating a cancer, comprising the modified three-helix bundle protein. Another embodiment provides a method of preventing and/or treating a cancer, comprising administering a pharmaceutically effective amount of the modified three-helix bundle protein to a subject in need of preventing and/or treating a cancer. The method may further comprises a step of identifying (selecting) a subject in need of preventing and/or treating a cancer, prior to the step of administering.

The pharmaceutical composition comprising a modified three-helix bundle protein may further comprise at least one additive selected from the group consisting of a pharmaceutically acceptable carriers, diluents, and excipients.

The pharmaceutically acceptable carrier to be included in the composition may be those commonly used for the formulation of antibodies, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The pharmaceutical composition may further include one or more selected from the group consisting of a lubricant, a wetting agent, a sweetener, a flavor enhancer, an emulsifying agent, a suspension agent, and preservative.

The pharmaceutical composition or the modified three-helix bundle protein may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the compositions may be administered using an optional device that enables an active substance to be delivered to target cells.

A suitable dosage or a suitable content of the modified three-helix bundle protein in the pharmaceutical composition may be prescribed in a variety of ways, depending on factors such as formulation methods, administration methods, age of patients, body weight, gender, pathologic conditions, diets, administration time, administration route, excretion speed, and reaction sensitivity. A desirable dosage of the modified three-helix bundle protein may be in the range of about 0.001 to 1000 mg/kg for an adult. For example, the suitable dosage of the modified three-helix bundle protein may be about 0.001 to about 1000 mg/kg, about 0.01 to about 100 mg/kg, or 0.1 to 50 mg/kg, per a day, but not be limited thereto. The term "pharmaceutically effective amount" used herein refers to an amount of the active ingredient (e.g., the modified three-helix bundle protein) exhibiting effects in preventing or treating cancer.

The pharmaceutical composition may be formulated with a pharmaceutically acceptable carrier and/or excipient into a unit or a multiple dosage form by a method easily carried out by a skilled person in the pertinent art. The dosage form may be a solution in oil or an aqueous medium, a suspension, syrup, an emulsifying solution, an extract, powder, granules, a tablet, or a capsule, and may further include a dispersing or a stabilizing agent.

In addition, the pharmaceutical composition or the modified three-helix bundle protein may be administered as an individual drug, or together with other drugs, and may be administered sequentially or simultaneously with pre-existing drugs.

The subject to which the pharmaceutical composition or the modified three-helix bundle protein is administered or to which the prevention and/treatment method is applied may be mammals, for example, primates such as humans and monkeys, or rodents such as rats and mice, or a cell or tissue separated therefrom, but are not be limited thereto. The subject may be a patient suffering from cancer, or a cell or tissue separated from the patient or artificially cultured, e.g., a cancer cell or cancer tissue.

The cancer may be a solid cancer or hematological cancer and for instance, may be, but not limited to, one or more selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and the like. The cancer may be a primary cancer or a metastatic cancer.

The prevention and/or treatment effects of the cancers may include effects of not only suppressing the growth of the cancer cells but also suppressing deterioration of cancers due to migration, invasion, and/or metastasis thereof.

Another embodiment provides a conjugate comprising (a) a modified three-helix bundle protein and (b) HDM2, HDMX or a combination of HDM2 and HDMX. In the conjugate, the HDM2, HDMX or combination of HDM2 and HDMX may be linked to the modified three-helix bundle protein at the position corresponding to the critical positions of N-terminal region of TAD of p53 and substituted with F, W, or L (i.e., $b^n$-$f^n$-$b^{n+1}$ and/or $f^m$-$c^{m+1}$-$f^{m+1}$, as described above).

Another embodiment provides a method of preparing a modified three-helix bundle protein, comprising substituting at least one amino acid of a three-helix bundle protein with different amino acid. The prepared modified three-helix bundle protein may be characterized by possessing a high binding ability to HDM2 and/or HDMX.

In particular, the method of preparing may comprise substituting (a) a region of a three-helix bundle protein corresponding to N-terminal region of TAD(transactivation domain) of p53, which is a binding site to HDM2 and HDMX, i.e., "QETFSDLWKLLPENNVLS" (SEQ ID NO: 2) or "ETFSDLWKLLPEN" (SEQ ID NO: 3) and/or (b) at least one selected from positions of a three-helix bundle protein corresponding to important residues of N-terminal region of TAD of p53 in binding with HDM2 and HDMX, phenylalanine (F) (the $5^{th}$ amino acid residue of SEQ ID NO: 2 or the $3^{rd}$ amino acid residue of SEQ ID NO: 3), tryptophan (W) (the $9^{th}$ amino acid residue of SEQ ID NO: 2 or the $7^{th}$ amino acid residue of SEQ ID NO: 3), and leucine (L) (the $12^{th}$ amino acid residue of SEQ ID NO: 2 or the $10^{th}$ amino acid residue of SEQ ID NO: 3), with the corresponding amino acids of the N-terminal region of TAD of p53 or the corresponding amino acid residue thereof (i.e., F, W and/or L).

The method of preparing may further comprise, prior to the step of substituting, determining (a) the region of a three-helix bundle protein corresponding to N-terminal region of TAD(transactivation domain) of p53, which is a binding site to HDM2 and HDMX, i.e., "QETFSDLWKLL-PENNVLS" (SEQ ID NO: 2) or "ETFSDLWKLLPEN" (SEQ ID NO: 3) and/or (b) at least one selected from positions of a three-helix bundle protein corresponding to important residues of N-terminal region of TAD of p53 in binding with HDM2 and HDMX, phenylalanine (F) (the $5^{th}$ amino acid residue of SEQ ID NO: 2 or the $3^{rd}$ amino acid residue of SEQ ID NO: 3), tryptophan (W) (the $9^{th}$ amino acid residue of SEQ ID NO: 2 or the $7^{th}$ amino acid residue of SEQ ID NO: 3), and leucine (L) (the $12^{th}$ amino acid residue of SEQ ID NO: 2 or the $10^{th}$ amino acid residue of SEQ ID NO: 3). The important residues of N-terminal region of TAD of p53 in binding with HDM2 and HDMX are as described above.

In particular, the method of preparing may comprise at least one amino acid substitution step selected from the group consisting of:

(1) a substitution of at least one selected from amino acid residues of a three-helix bundle protein, which are at the positions corresponding to amino acid residue 'F(phenylalanine)' at the $5^{th}$ position of SEQ ID NO: 2 or the $3^{rd}$ position of SEQ ID NO: 3 (e.g., the amino acid residues of a three-helix bundle protein may be at the position $b^n$ and/or $f^m$ as described above), with F(phenylalanine), H (histidine), or Y (tyrosine), for example, F, wherein the number of the amino acid residues corresponding to 'F' of SEQ ID NO: 2 or 3 present in the three-helix bundle protein may be one or at least two (e.g., 2 to 5 or 2 to 3) per a helix;

(2) a substitution of at least one selected from amino acid residues of a three-helix bundle protein, which are at the positions corresponding to amino acid residue 'W (tryptophan)' at the $9^{th}$ position of SEQ ID NO: 2 or the $7^{th}$ position of SEQ ID NO: 3 (e.g., the amino acid residues of a three-helix bundle protein may be at the position $f^n$ and/or $c^{m+1}$ as described above), with W(tryptophan), wherein the number of the amino acid residues corresponding to 'F' of SEQ ID NO: 2 or 3 present in the three-helix bundle protein may be one or at least two (e.g., 2 to 5 or 2 to 3) per a helix; and (3) a substitution of at least one selected from amino acid residues of a three-helix bundle protein, which are at the positions corresponding to amino acid residue 'L (leucine)' at the $12^{th}$ position of SEQ ID NO: 2 or the $10^{th}$ position of SEQ ID NO: 3 (e.g., the amino acid residues of a three-helix bundle protein may be at the position $b^{n+1}$ and/or $f^{m+1}$ as described above), with L(leucine), wherein the number of the amino acid residues corresponding to 'L' of SEQ ID NO: 2 or 3 present in the three-helix bundle protein may be one or at least two (e.g., 2 to 5 or 2 to 3) per a helix.

The positions of a three-helix bundle protein to be modified (substituted) (i.e., the positions corresponding to the amino acid residues F, W, and L present in the N-terminal region (e.g., SEQ ID NO: 2 or SEQ ID NO: 3) of TAD of p53 protein, which are critical in binding with HDM2 and/or HDMX) may be determined through an amino acid sequence alignment and/or a tertiary structure alignment with that of p53 protein by any conventional method. For example, the position to be modified may be at least one selected from the positions b, c, and f in a three-helix bundle protein, and more detailed matters are as described above.

In an embodiment, the method of preparing a modified three-helix bundle protein may comprise at least one amino acid substitution step selected from the group consisting of:

(i) a substitution of at least one amino acid selected from the positions 'b' in a three-helix bundle protein (the positions 'b' may be present in a three-helix bundle protein as many as the number of heptads comprised in the three-helix bundle protein) independently with phenylalanine (F) or leucine (L);

(ii) a substitution of at least one amino acid selected from the positions 'c' in a three-helix bundle protein (the positions 'c' may be present in a three-helix bundle protein as many as the number of heptads comprised in the three-helix bundle protein) independently with tryptophan (W); and (iii) a substitution of at least one amino acid selected from the positions 'f' in a three-helix bundle protein (the positions 'f' may be present in a three-helix bundle protein as many as the number of heptads comprised in the three-helix bundle protein) independently with tryptophan (W), phenylalanine (F) or leucine (L).

More detailed matters about the positions b, c, and f in a three-helix bundle protein and an amino acid to be substituted for each position are as described above.

In addition to the step of modification (substitution) at the positions corresponding to the amino acid residues F, W, and L of N-terminal region of TAD of p53 as described above, the method of preparing a modified three-helix bundle protein may comprise further amino acid substitution and/or insertion step, so that the modified three-helix bundle protein can avoid a structural conflict with HDM2 and/or HDMX thereby more strongly binding with HDM2 and/or HDMX.

For example, the positions in the modified three-helix bundle protein to be further modified (substituted and/or inserted) for avoiding physical conflict and/or strengthening the binding with HDM2 and/or HDMX may be at least one selected from positions e'. In addition to at least one selected from positions e', the positions in the modified three-helix bundle protein to be further modified may be at least one selected from positions 'b' other than the positions 'b' in the combination 'b-f-b' to be substituted with phenylalanine (F) or leucine (L), at least one selected from positions 'c' other than the positions 'c' in the combination 'f-c-f' to be substituted with tryptophan (W), at least one selected from positions 'g', or a combination thereof. The amino acids to be additionally substituted (i.e., inserted in replacement) for the original amino acids in a three-helix bundle protein may be independently selected from the group consisting of glycine (G), serine (S), alanine (A), glutamic acid (E), tyrosine (Y), tryptophan (W), and the like.

For example, in the additional amino acid substitutions, the additional step of substitution of amino acid may comprise at least one selected from the group consisting of the steps of:

i) substituting at least one amino acid at positions e' in a three-helix bundle protein independently with glycine (G), serine (S), alanine (A), tyrosine (Y), or tryptophan (W);

ii) substituting at least one amino acid at position 'b' in a three-helix bundle protein (wherein the position 'b' is other than the positions 'b' in the combination 'b-f-b' to be substituted with phenylalanine (F) or leucine (L)) independently with tyrosine (Y) or tryptophan (W);

iii) substituting at least one amino acid at positions 'c' in a three-helix bundle protein (wherein the positions 'c' is other than the positions 'c' in the combination 'f-c-f' to be substituted with tryptophan (W)) with glutamic acid (E); and/or iv) substituting at least one amino acid at positions 'g' in a three-helix bundle protein independently with glycine (G), serine (S), or alanine (A).

v) Optionally, the method of preparing a modified three-helix bundle protein may further comprise, in addition to the additional substituting step(s) as described above, a step of inserting one or at least two (e.g., 2-5 or 2-3) additional amino acid residues at C-terminus of the modified three-helix bundle protein. In this case, the amino acid to be additionally inserted in the modified three-helix bundle protein may be any amino acid with no limitation; for example, at least one independently selected from the group consisting of proline (P), serine (S), alanine (A), and the like, but not be limited thereto.

In one embodiment, the method of preparing a modified three-helix bundle protein may be conducted by using alpha3D protein (a3D; SEQ ID NO: 6) as a template. In this case, the method of preparing a modified three-helix bundle protein may comprise at least one amino acid substitution step selected from the groups consisting of:

1) substitutions of the amino acid at the $5^{th}$ position of SEQ ID NO: 6 (corresponding to the position 'b' of the first heptad (b¹)) with phenylalanine (F), the amino acid at the $9^{th}$ position of SEQ ID NO: 6 (corresponding to the position 'f' of the first heptad (f¹)) with tryptophan (W), and/or the amino acid at the $12^{th}$ position of SEQ ID NO: 6 (corresponding to the position 'b' of the second heptad (b²)) with leucine (L);

2) substitutions of the amino acid at the $12^{th}$ position of SEQ ID NO: 6 (corresponding to the position 'b' of the second heptad (b²)) with phenylalanine (F), the amino acid at the $16^{th}$ position of SEQ ID NO: 6 (corresponding to the position 'f' of the second heptad (f²)) with tryptophan (W), and/or the amino acid at the $19^{th}$ position of SEQ ID NO: 6 (corresponding to the position 'b' of the third heptad (b³)) with leucine (L);

3) substitutions of the amino acid at the $36^{th}$ position of SEQ ID NO: 6 (corresponding to the position 'b' of the fifth heptad (b⁵)) with phenylalanine (F), the amino acid at the $40^{th}$ position of SEQ ID NO: 6 (corresponding to the position 'f' of the fifth heptad (f⁵)) with tryptophan (W), and/or the amino acid at the $43^{rd}$ position of SEQ ID NO: 6 (corresponding to the position 'b' of the sixth heptad (b⁶)) with leucine (L);

4) substitutions of the amino acid at the $58^{th}$ position of SEQ ID NO: 6 (corresponding to the position 'f' of the seventh heptad (f⁷)) with phenylalanine (F), the amino acid at the $62^{nd}$ position of SEQ ID NO: 6 (corresponding to the position 'c' of the eighth heptad (c⁸)) with tryptophan (W), and/or the amino acid at the $65^{th}$ position of SEQ ID NO: 6 (corresponding to the position 'f' of the eighth heptad (f⁸)) with leucine (L); and 5) substitutions of the amino acid at the $65^{th}$ position of SEQ ID NO: 6 (corresponding to the position 'f' of the eighth heptad (f⁸)) with phenylalanine (F), the amino acid at the $69^{th}$ position of SEQ ID NO: 6 (corresponding to the position 'c' of the ninth heptad (c⁹)) with tryptophan (W), and/or the amino acid at the $72^{nd}$ position of SEQ ID NO: 6 (corresponding to the position 'f' of the ninth heptad (f⁹)) with leucine (L); or a combination of at least two of 1) to 5).

In another embodiment, the method of preparing a modified three-helix bundle protein using a3D protein (SEQ ID NO: 6) as a template may further comprise additional step of amino acid modification (substitution and/or insertion) in addition to the amino acid substitutions 1) to 5) as described above, and for example, the additional step of amino acid modification (substitution and/or insertion) may be at least one selected from the steps of:

6) a substitution of the amino acid at the $8^{th}$ position of SEQ ID NO: 6 (corresponding to the position 'e' of the first heptad) with serine (S) or alanine (A);

7) a substitution of the amino acid at the $13^{th}$ position of SEQ ID NO: 6 (corresponding to the position 'c' of the second heptad) with glutamic acid (E);

8) a substitution of the amino acid at the $15^{th}$ position of SEQ ID NO: 6 (corresponding to the position 'e' of the second heptad) with tyrosine (Y);

9) a substitution of the amino acid at the $39^{th}$ position of SEQ ID NO: 6 (corresponding to the position e' of the fifth heptad) with tyrosine (Y);

10) a substitution of the amino acid at the $61^{st}$ position of SEQ ID NO: 6 (corresponding to the position 'b' of the eighth heptad) with tyrosine (Y);

11) a substitution of the amino acid at the $68^{th}$ position of SEQ ID NO: 6 (corresponding to the position 'b' of the ninth heptad) with tyrosine (Y);

12) a substitution of the amino acid at the $73^{rd}$ position of SEQ ID NO: 6 (corresponding to the position 'g' of the ninth heptad) with serine (S); and 13) an insertion of proline (P) at the C-terminus of SEQ ID NO: 6 (corresponding to the $74^{th}$ position of SEQ ID NO: 6); or a combination of at least two substitutions selected from substitutions 6) to 13).

Another embodiment provides a polynucleotide encoding the modified three-helix bundle protein, a recombinant vector comprising the polynucleotide, and a recombinant cell comprising the polynucleotide or the recombinant vector.

The polynucleotide encoding the modified three-helix bundle protein may be one encoding the amino acid sequence of SEQ ID NO: 7, 8, 9, 10, 11, 12, 13, 14, 15, or 16.

The term "vector" used herein refers to a means for expressing a target gene in a host cell. For example, it includes a plasmid vector, a cosmid vector, and a virus vector such as a bacteriophage vector, an adenovirus vector, a retrovirus vector and an adeno-associated virus vector. Suitable recombinant vectors may be constructed by manipulating plasmids often used in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, and the like), a phage (for example, λgt4λB, λ-Charon, λΔz1, M13, and the like), or a virus (for example, SV40, and the like), but not be limited thereto.

In the recombinant vector, the polynucleotides may be operatively linked to a promoter. The term "operatively linked" used herein refers to a functional linkage between a nucleotide expression regulating sequence (for example, a promoter sequence) and other nucleotide sequences. Thus, the regulating sequence may regulate the transcription and/or translation of the other nucleotide sequences by being operatively linked.

The recombinant vector may be constructed for cloning or expression. The expression vector may be any ordinary vectors known in the pertinent art for expressing an exogenous protein in plants, animals, or microorganisms. The recombinant vector may be constructed using various methods known in the art.

The recombinant vector may be constructed using a prokaryotic cell or a eukaryotic cell as a host. For example, when a prokaryotic cell is used as a host cell, the expression vector used generally includes a strong promoter capable of initiating transcription (for example, pL^λ promoter, CMV promoter, trp promoter, lac promoter, tac promoter, T7 promoter, and the like), a ribosome binding site for initiating translation, and a transcription/translation termination sequence. When a eukaryotic cell is used as a host cell, the vector used generally includes the origin of replication acting in the eukaryotic cell, for example, a f1 replication origin, a SV40 replication origin, a pMB 1 replication origin, an adeno replication origin, an AAV replication origin, or a BBV replication origin, but is not limited thereto. A promoter in an expression vector for a eukaryotic host cell may be a promoter derived from the genomes of mammalian cells (for example, a metallothionein promoter, and the like) or a promoter derived from mammalian viruses (for example, an adenovirus late promoter, a vaccinia virus 7.5K promoter, a SV40 promoter, a cytomegalovirus promoter, a tk promoter of HSV, and the like). A transcription termination sequence in an expression vector for a eukaryotic host cell may be, in general, a polyadenylation sequence.

The recombinant cell may be one obtained by transfecting the recombinant vector into a suitable host cell. Any host cells known in the pertinent art to enable stable and continuous cloning or expression of the recombinant vector may be used as the hose cell. Suitable prokaryotic host cells may be one or more selected from *E. coli* JM109, *E. coli* BL21, *E. coli* RR1, *E. coli* LE392, *E. coli* B, *E. coli* X 1776, *E. coli* W3110, *Bacillus* species strains such as *Bacillus subtillis*, or *Bacillus thuringiensis*, intestinal bacteria and strains such as *Salmonella typhymurum, Serratia marcescens*, and various *Pseudomonas* species. Suitable eukaryotic host cells to be transformed may be one or more selected from yeasts, such as *Saccharomyces cerevisiae*, insect cells, plant cells, and animal cells, for example, Sp2/0, Chinese hamster ovary (CHO) K1, CHO DG44, PER.C6, W138, BHK, COS-7, 293, HepG2, Huh7, 3T3, RIN, and MDCK cell lines, but not be limited thereto.

The polynucleotide or the recombinant vector including the same may be transferred (transfected) into a host cell by using known transfer methods. Suitable transfer methods for prokaryotic host cells may include a method using $CaCl_2$ and electroporation. Suitable transfer methods for eukaryotic host cells may include microinjection, calcium phosphate precipitation, electroporation, liposome-mediated transfection, and gene bombardment, but are not limited thereto.

A transformed or transfected host cell may be selected using a phenotype expressed by a selected marker by any methods known in the art. For example, if the selected marker is a gene that is resistant to a specific antibiotic, a transformed or transfected cell may be easily selected by being cultured in a medium including the antibiotic.

The modified three-helix bundle protein provided herein has high binding ability to HDM2/HDMX, thereby being useful in treating diseases associated with HDM2/HDMX activation such as cancer. When conjugated with a cell penetrating peptide, the modified three-helix bundle protein can be more efficiently delivered to cancer cells, thereby exhibiting increased anticancer effects.

EXAMPLES

Hereafter, the present invention will be described in detail by examples.

The following examples are intended merely to illustrate the invention and are not construed to restrict the invention.

Example 1: Preparation of Modified Three-Helix Bundle Proteins

Modified three-helix bundle proteins were designed as following Tables 1-3:

TABLE 1

| heptad position | | | | | | a | b | c | d | e | f | g | a | b | c | d | e | f | g | a | b | c | d |
|---|---|---|---|---|---|---|---|---|---|---|---|---|---|---|---|---|---|---|---|---|---|---|---|
| residue number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| α3D | M | G | S | W | A | E | F | K | Q | R | L | A | A | I | K | T | R | L | Q | A | L | G | G | S |
| M11 | M | G | S | W | A | E | F | S | Q | R | L | F | A | I | Y | W | R | L | L | A | L | G | G | S |
| M12 | M | G | S | W | A | E | F | K | Q | R | L | A | A | I | K | T | R | L | Q | A | L | G | G | S |
| M13 | M | G | S | W | A | E | F | K | Q | R | L | A | A | I | K | T | R | L | Q | A | L | G | G | S |
| M14 | M | G | S | W | A | E | F | S | Q | R | L | F | A | I | Y | W | R | L | L | A | L | G | G | S |
| M15 | M | G | S | W | A | E | F | S | Q | R | L | F | A | I | Y | W | R | L | L | A | L | G | G | S |
| M16 | M | G | S | W | A | E | F | K | Q | R | L | A | A | I | K | T | R | L | Q | A | L | G | G | S |
| M17 | M | G | S | W | A | E | F | S | Q | R | L | F | A | I | Y | W | R | L | L | A | L | G | G | S |
| P53 | | | | | | | | E | T | F | S | D | L | W | K | L | L | P | E | N | | | | |
| pDIQ | | | | | | | | E | T | F | E | H | W | W | S | Q | L | L | S | — | | | | |
| pMI | | | | | | | | T | S | F | A | E | Y | W | N | L | L | S | P | — | | | | |
| M21 | M | G | S | W | F | E | F | A | W | R | L | L | E | I | K | T | A | L | Q | A | L | G | G | S |
| M23 | M | G | S | W | A | E | F | K | Q | R | L | A | A | I | K | T | R | L | Q | A | L | G | G | S |
| M25 | M | G | S | W | F | E | F | A | W | R | L | L | E | I | K | T | R | L | Q | A | L | G | G | S |
| pMI | | T | S | F | A | E | Y | W | N | L | L | S | P | | | | | | | | | | | |
| pDIQ | | E | T | F | E | H | W | W | S | Q | L | L | S | | | | | | | | | | | |
| P53 | S | Q | E | T | F | S | D | L | W | K | L | L | P | E | N | N | V | L | S | | | | | |

TABLE 2

| heptad position | e | f | g | a | b | c | d | e | f | g | a | b | c | d | e | f | g | a | b | c | d |
|---|---|---|---|---|---|---|---|---|---|---|---|---|---|---|---|---|---|---|---|---|---|
| residue number | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 |
| α3D | E | A | E | L | A | A | F | E | K | E | I | A | A | F | E | S | E | L | Q | A | Y | K | G | K | G |
| M11 | E | A | E | L | A | A | F | E | K | E | I | A | A | F | E | S | E | L | Q | A | Y | K | G | K | G |
| M12 | E | A | E | L | A | A | F | E | K | E | I | F | A | F | Y | W | E | L | L | A | Y | K | G | K | G |
| M13 | E | A | E | L | A | A | F | E | K | E | I | A | A | F | E | S | E | L | Q | A | Y | K | G | K | G |
| M14 | E | A | E | L | A | A | F | E | K | E | I | F | A | F | Y | W | E | L | L | A | Y | K | G | K | G |
| M15 | E | A | E | L | A | A | F | E | K | E | I | A | A | F | E | S | E | L | Q | A | Y | K | G | K | G |
| M16 | E | A | E | L | A | A | F | E | K | E | I | F | A | F | Y | W | E | L | L | A | Y | K | G | K | G |
| M17 | E | A | E | L | A | A | F | E | K | E | I | F | A | F | Y | W | E | L | L | A | Y | K | G | K | G |
| P53 | | | | | | | | E | T | F | S | D | L | W | K | L | L | P | E | N | | | | | |
| pDIQ | | | | | | | | E | T | F | E | H | W | W | S | Q | L | L | S | — | | | | | |
| pMI | | | | | | | | T | S | F | A | E | Y | W | N | L | L | S | P | — | | | | | |
| M21 | E | A | E | L | A | A | F | E | K | E | I | A | A | F | E | S | E | L | Q | A | Y | K | G | K | G |
| M23 | E | A | E | L | A | A | F | E | K | E | I | A | A | F | E | S | E | L | Q | A | Y | K | G | K | G |
| M25 | E | A | E | L | A | A | F | E | K | E | I | A | A | F | E | S | E | L | Q | A | Y | K | G | K | G |
| pMI | | | | | | | | | | | | | | | | | | | | | | | | | |
| pDIQ | | | | | | | | | | | | | | | | | | | | | | | | | |
| P53 | | | | | | | | | | | | | | | | | | | | | | | | | |

TABLE 3

| heptad position | e | f | g | a | b | c | d | e | f | g | a | b | c | d | e | f | g | a | b | c | d | e | f | g |
|---|---|---|---|---|---|---|---|---|---|---|---|---|---|---|---|---|---|---|---|---|---|---|---|---|
| residue number | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 |
| α3D | N | P | E | V | E | A | L | R | K | E | A | A | A | I | R | D | E | L | Q | A | Y | R | H | N | — |
| M11 | N | P | E | V | E | A | L | R | K | E | A | A | A | I | R | D | E | L | Q | A | Y | R | H | N | — |
| M12 | N | P | E | V | E | A | L | R | K | E | A | A | A | I | R | D | E | L | Q | A | Y | R | H | N | — |
| M13 | N | P | E | V | E | A | L | R | K | E | A | A | A | I | R | F | E | L | Y | W | Y | R | L | S | P |
| M14 | N | P | E | V | E | A | L | R | K | E | A | A | A | I | R | D | E | L | Q | A | Y | R | H | N | — |
| M15 | N | P | E | V | E | A | L | R | K | E | A | A | A | I | R | F | E | L | Y | W | Y | R | L | S | P |
| M16 | N | P | E | V | E | A | L | R | K | E | A | A | A | I | R | F | E | L | Y | W | Y | R | L | S | P |
| M17 | N | P | E | V | E | A | L | R | K | E | A | A | A | I | R | F | E | L | Y | W | Y | R | L | S | P |
| P53 | | | | | | | | E | T | F | S | D | L | W | K | L | L | P | E | N | | | | | |
| pDIQ | | | | | | | | E | T | F | E | H | W | W | S | Q | L | L | S | — | | | | | |
| pMI | | | | | | | | T | S | F | A | E | Y | W | N | L | L | S | P | — | | | | | |
| M21 | N | P | E | V | E | A | L | R | K | E | A | A | A | I | R | D | E | L | Q | A | Y | R | H | N | — |
| M23 | N | P | E | V | E | A | L | R | F | E | A | Y | W | I | R | L | E | L | Q | A | Y | R | H | N | — |
| M25 | N | P | E | V | E | A | L | R | F | E | A | Y | W | I | R | L | E | L | Q | A | Y | R | H | N | — |
| pMI | | | | | | | | T | S | F | A | E | Y | W | N | L | L | S | P | | | | | | |
| pDIQ | | | | | | | | E | T | F | E | H | W | W | S | Q | L | L | S | | | | | | |
| P53 | | | | | | S | Q | E | T | F | S | D | L | W | K | L | L | P | E | N | N | V | L | S | |

(pDIQ: PDB code 3JZS; pMI: PDB code 3EQS)

The amino acid sequences of M11, M12, M13, M14, M15, M16, M17, M21, M23 and M25 in Tables 1 to 3 are described in SEQ ID NOs: 7 to 16, respectively. The amino acid sequences of α3D, p53, pDIQ, and pMI are provided in SEQ ID NOs: 6, 2, 5, and 4, respectively.

In Tables 1 to 3, the residues in boxes indicate positions of modification (substitution) for binding to HDM2 and/or HDMX, and the residues in circles indicate positions of modification (substitution) for more enhancing the binding to HDM2 and/or HDMX and/or avoiding structural collision with HDM2 and/or HDMX.

Figure 2:
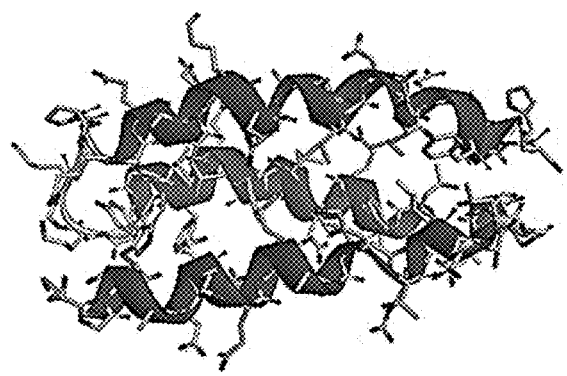
FIG. 2 shows the structure of alpha3D (α3D; SEQ ID NO: 6) and the amino acid sequence of a representative single stranded three-helix bundle protein used as a template.
Figure 3:
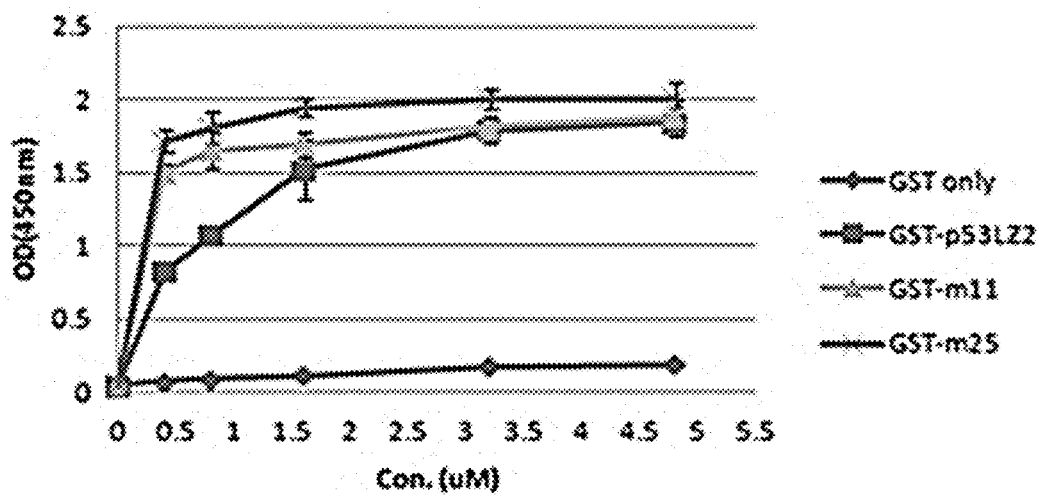
FIG. 3 is a graph showing the binding affinity of a modified three-helix bundle protein to the MDMX N-terminal domain (MDMX-NTD).
Figure 4:
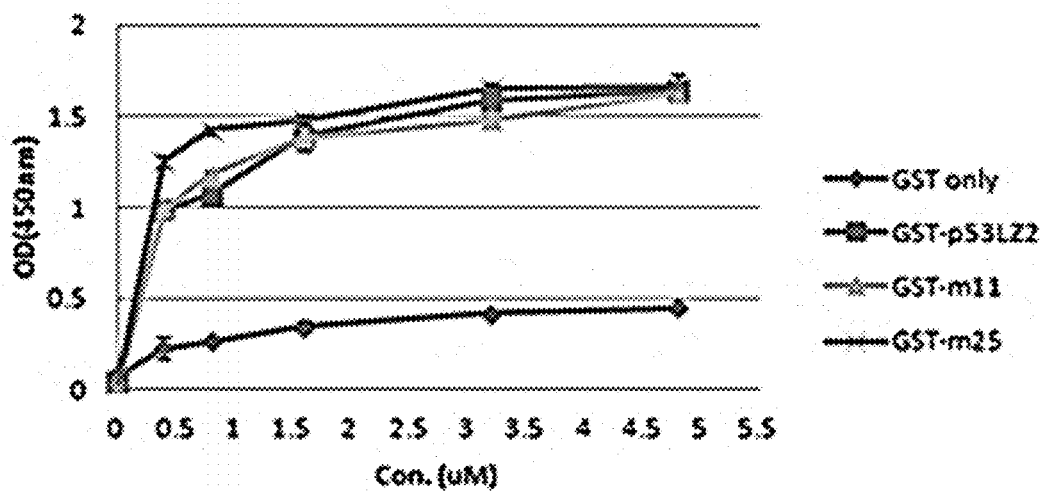
FIG. 4 is a graph showing the binding affinity of a modified three-helix bundle protein to full-length MDM2.
Figure 5:
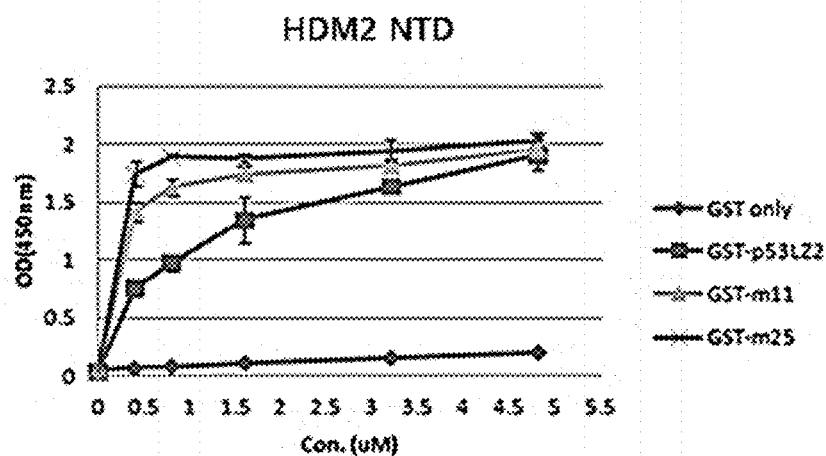
FIG. 5 is a graph showing the binding affinity of a modified three-helix bundle protein to the MDM2 N-terminal domain (MDM2-NTD).
Figure 6:
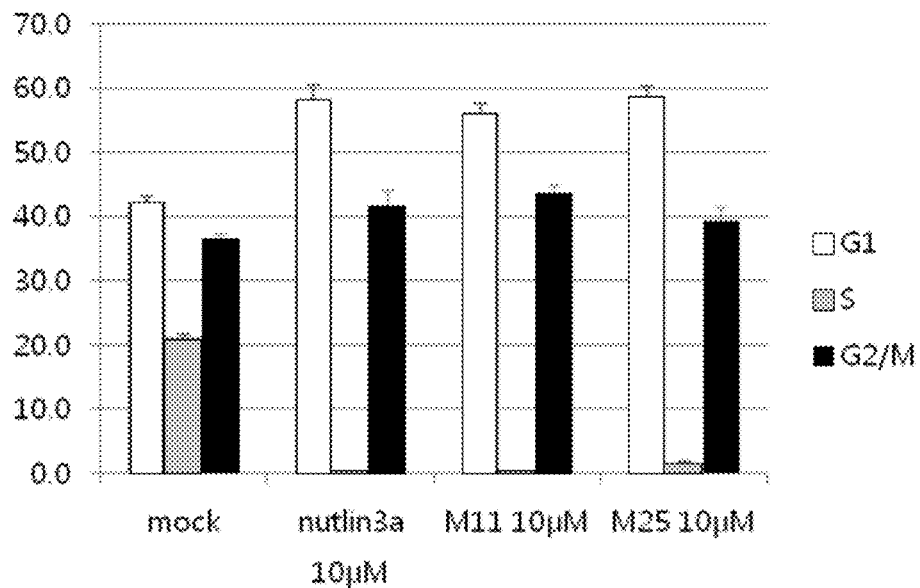
FIG. 6 is a graph showing the ratio of the number of osteosarcoma cells present in each phase cell cycle compared to the total number of cells when the osteosarcoma cells are treated with a modified three-helix bundle protein.
Figure 7:
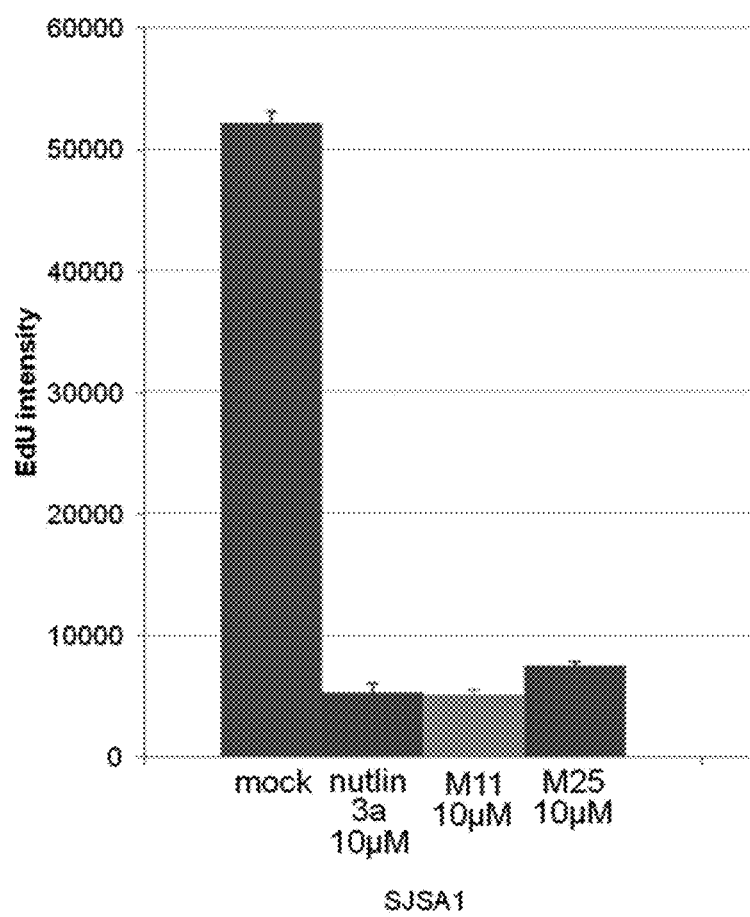
FIG. 7 is a graph showing the number of osteosarcoma cells present in S-phase of the cell cycle by Eud EdU intensity when the osteosarcoma cells are treated with a modified three-helix bundle protein

In particular, a representative example of three-helix bundle proteins, a3D protein was employed as a template. a3D protein has the amino acid sequence of SEQ ID NO: 6, and single stranded 3-helix bundle structure (see FIG. 2).

The three-dimensional structures of a3D (SEQ ID NO: 6), wild-type p53 (SEQ ID NO: 1), pMI (HDM2 & HDMX high affinity peptide; TSFAEYWNLLSP; SEQ ID NO: 4), and pDIQ (ETFEHWWSQLLS: SEQ ID NO: 5) were analyzed and compared to one another, thereby determining i) a region of a3D protein which corresponds to N-terminal region, SQETFSDLWKLLPENNVLS(SEQ ID NO: 2) or ETFSDLWKLLPEN(SEQ ID NO: 3), of transactivation domain (TAD; SEQ ID NO: 5) of p53, where recognized by HDM2 and/or HDMX, and then, ii) optimal positions of a3D protein corresponding to residues F ($5^{th}$ residue of SEQ ID NO: 2 or $3^{rd}$ residue of SEQ ID NO: 3), W ($9^{th}$ residue of SEQ ID NO: 2 or $7^{th}$ residue of SEQ ID NO: 3), and L ($12^{th}$ residue of SEQ ID NO: 2 or $10^{th}$ residue of SEQ ID NO: 3), which are the most critical residues of N-terminal region of TAD of P53 for binding with HDM2 and/or HDMX, for grafting of the residues into a3D protein. The determined positions of a3D protein for grafting of residues are positions "f", "b" and/or "c", in heptad structure. a3D proteins includes 9 heptads in total, wherein at least one position selected from nine "f" positions, nine "b" positions, and nine "c" positions is substituted with one selected from the residues F, W, and L, which is a residue of the N-terminal region of TAD of p53 corresponding to the position of a3D to be substituted (see residues in box in Table 1). In addition, at least one position of a3D protein capable of avoiding structural collision with HDM2/HDMX was determined through a docking study with HDM2/HDMX, and substituted (see residues in circle in Table 1), to contribute to more enhanced binding with HDM2/HDMX. According to the above, modified proteins of three-helix bundle proteins, M11-M17, M21, M23, and M25, which are a3D variants, were prepared.

Example 2: Binding Strength of Modified Three-Helix Bundle Proteins to HDM2/HDMX The binding strength of the modified three-helix bundle proteins prepared in Example 1 was examined by ELISA.

In particular, each of full-length HDM2 (NP 002383.2), HDM2 N-terminal domain (NTD; the region from $1^{st}$ to $125^{th}$ amino acids of NP 002383.2), full-length HDMX (NP_001191100.1), and HDMX NTD (the region from $1^{st}$ to $132^{nd}$ amino acids of NP_001191100.1) was diluted to the concentration of 20 μg/ml with coating buffer (pH 9.6; 0.05M carbonate-bicarbonate buffer, pH9.6; Sigma-Aldrich), and coated on 96 well (Nunc, Maxisorp). The well was incubated overnight at 4° C. Thereafter, bindings between other proteins were blocked with 300 ul of 3% skim milk w/PBS-T (at room temperature for 3 hours). The 96 well plate was washed with 200 uL of PBS-T and treated with GST-M11 (SEQ ID NO: 7) or GST-M25 (SEQ ID NO: 16) at a concentration of 0, 0.5, 1, 1.5, 2, 2.5, 3, 3.5, 4, 4.5, 5, or 5.5 uM (micromole). The GST protein was produced from GST cds included in pGEX-4T3 vector purchased from GE healthcare.

One hour after, the plate was washed with 300 uL of PBS-T, and treated with 100 uL of HRP conjugated-anti-GST antibody (Abcam, 1:2000). After the reaction at room temperature for one hour, the plate was treated with TMB substrate (Pierce, 100 uL) and left for 5 minute until coloring reaction occur, and then, treated with stop solution (Pierce, 100 uL). Thereafter, absorbance at 450 nm was measured using microwell reader (Molecular Device, 340PC384).

For comparison, the same experiments were performed using GST protein only (negative control) and GST-p53LZ2 (positive control: which is another p53 mimetic generated from a leucine zipper dimer constructed of alpha helix of SEQ ID NO: 17, wherein the positions corresponding to residues F, W, and L of N-terminal region of TAD of p53, which are determined by amino acid sequence and tertiary structure alignment with p53, are substituted with F, W, and L, respectively).

The obtained results were shown in FIGS. 3 to 5. FIG. 3 shows binding strength to HDMX NTD, FIG. 4 shows binding strength to full-length HDM2, and FIG. 5 shows binding strength to HDM2 NTD. As shown in FIGS. 3 to 5, the binding strength of the modified three-helix bundle protein (M11, M25) to HDM2 and/or HDMX is considerably higher than that of the negative control, and similar to or higher than that of the positive control, which is another p53 mimetic p53LZ2. These results suggest that the modified three-helix bundle proteins may compete with p53 for binding to HDM2 and/or HDMX, and is capable of binding to HDM2 and/or HDMX at high efficiency, thereby inhibiting the binding between p53 and HDM2 and/or HDMX and thus, effectively inhibiting degradation of p53.

Example 3: Cell Cycle Arrest Effect of Modified Three-Helix Bundle Proteins

In this example, it was examined if the modified three-helix bundle proteins prepared in Example 3 can induce G1 and G2/M phase cell cycle arrest in SJSA-1 (p53+/+; ATCC), which is an osteosarcoma cell line expressing wild-type p53.

In particular, SJSA1 cells were treated with the modified three-helix bundle protein M11 or M25 at the concentration of 10 uM for 24 hours, and stained with EdU (Edu staining kit, Life Technology Inc.) and Hoescht 33342 (Life Technology Inc.). Among the cells, at least 1000 cells were analyzed by imaging with incell analyzer 6000 (Ge Healthcare) and incell communicator (GE Healthcare). For comparison, the same experiment using Nutlin 3a (Sigma) at the concentration of 10 uM was performed as a positive control.

The imaging results were analyzed by measuring the intensities of EdU (S phase indicator) and Hoescht33342 (DNA content indicator) at single cell level, and determining each population by measuring intensity of Hoescht33342 (DNA content indicator) and EdU (S phase indicator) at single cell level, thereby measuring ratio of cells at each cell cycle phase. The obtained population of each cell cycle phase was shown in FIG. 6, and the S phase measured by EdU uptake amount (EdU intensity) was shown in FIG. 7. FIG. 6 shows the cell cycle population by each ratio (%: number of cells in each cell cycle phase/number of total cells). Such results indicate that the level of cell cycle arrest at G1 phase by treatment of the modified three-helix bundle protein (M11, M25) is similar to that of the positive control (nutlin3a). G2/M is considered as a course progressing to G1 phase. In addition, FIG. 7 shows the level (cell number) of total cells at S phase measured by Eud intensity, and indicates that the treatment of modified three-helix bundle proteins (M11, M25) lead to decrease in level (cell number) of cells at S phase compared to that of control (Mock), similar to the positive control (nutlin3a).

Example 4: Cancer Cell Proliferation Inhibition Effect of Modified Three-Helix Bundle Proteins The effects of the modified three-helix bundle proteins prepared in Example 1 to inhibit cancer cell proliferation was examined in SJSA-1 (p53+/+; ATCC), which is an osteosarcoma cell line expressing wild-type p53.

Cells were seeded in 10% FBS supplemented RPMI medium (Gibco) or DMEM medium (Gibco) in 96-well plate so that $1\times10^3$ cells were included in each well, and at the next day, the cells were treated with active material, i.e., TAT-M11 (produced by coupling TAT(RKKRRQRRR; SEQ ID NO: 18) to the N-terminus of modified three-helix bundle protein M11 prepared in Example 1), TAT-M25 (produced by coupling TAT(RKKRRQRRR; SEQ ID NO: 18) to the N-terminus of modified three-helix bundle protein M25 prepared in Example 1), or Nutlin-3 (Roche; positive control) at the amount of 100 uL per each well, wherein the concentration of each active material is 0, 0.16, 0.31, 0.63, 1.25, 2.50, 5.00, or 10.00 uM (micromole). The cells were cultured in $CO_2$ incubator under the conditions of 37° C., and $CO_2$ 5%, for 5 days. 80 uL of CellTiter-Glo reagent (Promega) was added to each well, and luminescence was measured with EnVision Multilabel Reader (PerkinElmer), to measure cell viability. The cell viability is indicated by a relative value to that of non-treated cells ("1.0").

Figure 8:
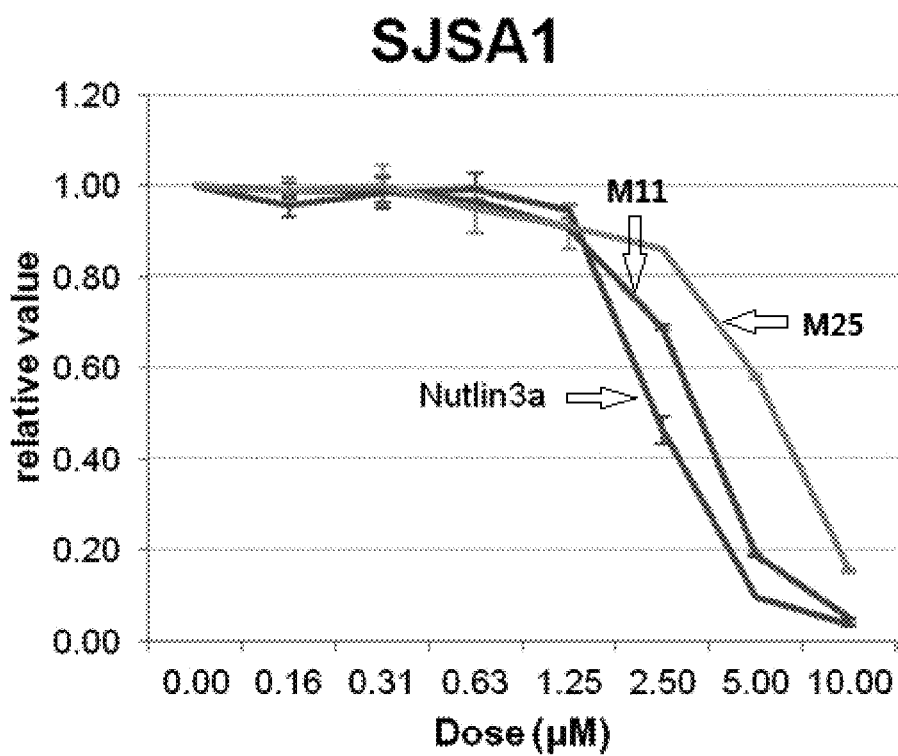
FIG. 8 is a graph showing cancer cell proliferation inhibition effects of a modified three-helix bundle protein.

The obtained results were shown in FIG. 8. As shown in FIG. 8, both of the modified three-helix bundle protein M11 and M25 exhibit considerably high cancer cell proliferation inhibition effect (cancer cell death rate of at least 90% and at least 80%, respectively, at the concentration of 10.00 uM), which is equal to that of Nutlin-3 undergoing clinical testing.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A three-helix bundle protein wherein
the three-helix bundle protein comprises at least two heptads in which the amino acids of the heptad correspond to positions a, b, c, d, e, f, and g; m and n are consecutive integers representing the position of the consecutive heptad in order from N-terminus to C terminus of the three-helix protein, and are independently selected from 1-20; and wherein:
the positions b'', f', and b''$^{+1}$ of the three-helix bundle protein is phenylalanine, tryptophan, and leucine, in order;
the positions f', c'$^{m+1}$, and f'$^{m+1}$ of the three-helix bundle protein is phenylalanine, tryptophan, and leucine, in order; or
a combination thereof.

2. The three-helix bundle protein of claim 1, wherein
i) position 'e' in each heptad of the three-helix bundle protein is glycine, serine, alanine, tyrosine, or tryptophan;
ii) position 'b' in each heptad of the three-helix bundle protein is independently tyrosine or tryptophan, wherein the position 'b' is not the position 'b''' or 'b''$^{+1}$' which is phenylalanine or leucine;
iii) position 'c' in each heptad of the three-helix bundle protein is glutamic acid, wherein the position 'c' is not the positions 'c''' or 'c'$^{m+1}$' which is tryptophan;
iv) position 'g' in each heptad of the three-helix bundle protein is glycine, serine, or alanine;
v) 2 to 5 amino acid residues are added to the C-terminus of a three-helix bundle protein, or
a combination thereof.

3. The three-helix bundle protein of claim 1, wherein the three-helix bundle protein comprises SEQ ID NO: 6 in which:
a) the amino acid at the position of SEQ ID NO: 6, corresponding to the 5th position of SEQ ID NO: 2 or the 3rd position of SEQ ID NO: 3, is substituted with phenylalanine;
b) the amino acid at the position of SEQ ID NO: 6, corresponding to the 9th position of SEQ ID NO: 2 or the 7th position of SEQ ID NO: 3, is substituted with tryptophan,
c) the amino acid at the position of SEQ ID NO: 6, corresponding to the 12th position of SEQ ID NO: 2 or the 10th position of SEQ ID NO: 3, is substituted with leucine, or
a combination of at least two of a) to c).

4. The three-helix bundle protein of claim 3, wherein the three-helix bundle protein comprises SEQ ID NO: 6 in which:
1) the amino acid at the 5th position of SEQ ID NO: 6 is substituted with phenylalanine, the amino acid at the 9th position of SEQ ID NO: 6 is substituted with tryptophan, and/or the amino acid at the 12th position of SEQ ID NO: 6 is substituted with leucine;
2) the amino acid at the 12th position of SEQ ID NO: 6 is substituted with phenylalanine, the amino acid at the 16th position of SEQ ID NO: 6 is substituted with tryptophan, and/or the amino acid at the 19th position of SEQ ID NO: 6 is substituted with leucine;
3) the amino acid at the 36th position of SEQ ID NO: 6 is substituted with phenylalanine, the amino acid at the 40th position of SEQ ID NO: 6 is substituted with tryptophan, and/or the amino acid at the 43rd position of SEQ ID NO: 6 is substituted with leucine;
4) the amino acid at the 58th position of SEQ ID NO: 6 is substituted with phenylalanine, the amino acid at the 62nd position of SEQ ID NO: 6 is substituted with tryptophan, and/or the amino acid at the 65th position of SEQ ID NO: 6 is substituted with leucine;
5) the amino acid at the 65th position of SEQ ID NO: 6 is substituted with phenylalanine, the amino acid at the 69th position of SEQ ID NO: 6 is substituted with tryptophan, and/or the amino acid at the 72nd position of SEQ ID NO: 6 is substituted with leucin; or
a combination of at least two of 1) to 5).

5. The three-helix bundle protein of claim 4, wherein
1) the amino acid at the 8th position of SEQ ID NO: 6 is substituted with serine or alanine;
2) the amino acid at the 13th position of SEQ ID NO: 6 is substituted with glutamic acid;
3) the amino acid at the 15th position of SEQ ID NO: 6 is substituted with tyrosine;
4) the amino acid at the 39th position of SEQ ID NO: 6 is substituted with tyrosine;
5) the amino acid at the 61st position of SEQ ID NO: 6 is substituted with tyrosine;
6) the amino acid at the 68th position of SEQ ID NO: 6 is substituted with tyrosine;
7) the amino acid at the 73rd position of SEQ ID NO: 6 is substituted with serine;
8) proline (P) is inserted at the 74th position of SEQ ID NO: 6; or
a combination thereof.

6. The three-helix bundle protein of claim 3, comprising the amino acid sequence of SEQ ID NO: 7, 8, 9, 10, 11, 12, 13, 14, 15, or 16.

7. The three-helix bundle protein of claim 1, further comprising at least one cell penetrating peptide selected from the group consisting of:

TAT, (SEQ ID NO: 18)

MTS, (SEQ ID NO: 19)

peptide fragments comprising 7 to 16 consecutive amino acids of the MTS, and
fusion peptides comprising the MTS or peptide fragment and a nuclear localization sequence of SEQ ID NO: 22, 23, 24, 25, or 26.

8. The three-helix bundle protein of claim 3, further comprising at least one cell penetrating peptide selected from the group consisting of:

TAT, (SEQ ID NO: 18)

MTS, (SEQ ID NO: 19)

peptide fragments comprising 7 to 16 consecutive amino acids of the MTS, and fusion peptides comprising the MTS or peptide fragment and a nuclear localization sequence of SEQ ID NO: 22, 23, 24, 25, or 26.

9. A polynucleotide encoding the three-helix bundle protein of claim 1.

10. A recombinant vector comprising the polynucleotide of claim 9.

11. A recombinant cell line comprising the recombinant vector of claim 10.

12. A pharmaceutical composition comprising the three-helix bundle protein of claim 1 or polynucleotide encoding same, optionally in a vector or recombinant cell.

13. A method of treating a cancer in a subject, comprising administering the three-helix bundle protein of claim 1 to the subject.

14. A method of treating a cancer in a subject, comprising administering the three-helix bundle protein of claim 3 to the subject.

15. A protein conjugate comprising
(1) the three-helix bundle protein of claim 1, and
(2) HDM2, HDMX or a combination of HDM2 and HDMX.

16. A protein conjugate comprising
(1) the three-helix bundle protein of claim 3, and
(2) HDM2, HDMX or a combination of HDM2 and HDMX.

17. A method of preparing a three-helix bundle protein, comprising at least one step of:
a) substituting an amino acid residue at a position of a naturally occurring three-helix bundle protein that corresponds to phenylalanine at the 5th position of SEQ ID NO: 2 or the 3rd position of SEQ ID NO: 3, with phenylalanine;
b) substituting an amino acid residue at a position of a naturally occurring three-helix bundle protein that corresponds to tryptophan at the 9th position of SEQ ID NO: 2 or the 7th position of SEQ ID NO: 3, with tryptophan; and
c) substituting an amino acid residue at a position of a naturally occurring three-helix bundle protein that protein that corresponds to leucine at the 12th position of SEQ ID NO: 2 or the 10th position of SEQ ID NO: 3, with leucine.

18. A three-helix bundle protein comprising
MGSWX$_1$EFX$_2$X$_3$R LX$_4$X$_5$IX$_6$X$_7$RLX$_8$A LGGSEAELAA FEKEIX$_9$AFX$_{10}$X$_{11}$ ELX$_{12}$AYKGKGN PEVEALRX$_{13}$EA X$_{14}$X$_{15}$IRX$_{16}$ELX$_{17}$X$_{18}$Y RX$_{19}$X$_{20}$X$_{21}$ (SEQ ID NO: 28),
wherein, X$_1$ is A or F; X$_2$ is K, S, or A; X$_3$ is Q or W; X$_4$ is A, F, or L; X$_5$ is A or E; X$_6$ is K or Y; X$_7$ is T or W; X$_8$ is Q or L; X$_9$ is A or F; X$_{10}$ is E or Y; X$_{11}$ is S or W; X$_{12}$ is Q or L; X$_{13}$ is K or F; X$_{14}$ is A or Y; X$_{15}$ is A or W; X$_{16}$ is D, F, or L; X$_{17}$ is Q or Y; X$_{18}$ is A or W; X$_{19}$ is H or L; X$_{20}$ is N or S; and X$_{21}$ is absent or P;
provided that the three helix bundle protein does not comprise SEQ ID NO: 6.

* * * * *

SEQUENCE LISTING

<160> NUMBER OF SEQ ID NOS: 28

<210> SEQ ID NO 1
<211> LENGTH: 393
<212> TYPE: PRT
<213> ORGANISM: Artificial Sequence
<220> FEATURE:
<223> OTHER INFORMATION: Synthetic p53

<400> SEQUENCE: 1

```
Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
     50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125
```

```
Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 2
<211> LENGTH: 19
<212> TYPE: PRT
<213> ORGANISM: Artificial Sequence
<220> FEATURE:
<223> OTHER INFORMATION: Synthetic N-terminal TAD(transactivation
      domain) of p53

<400> SEQUENCE: 2

Ser Gln Glu Thr Phe Ser Asp Leu Trp Lys Leu Leu Pro Glu Asn Asn
  1               5                  10                  15

Val Leu Ser

<210> SEQ ID NO 3
<211> LENGTH: 13
<212> TYPE: PRT
<213> ORGANISM: Artificial Sequence
<220> FEATURE:
<223> OTHER INFORMATION: Synthetic N-terminal TAD(transactivation
      domain) of p53

<400> SEQUENCE: 3

Glu Thr Phe Ser Asp Leu Trp Lys Leu Leu Pro Glu Asn
```

<210> SEQ ID NO 4
<211> LENGTH: 12
<212> TYPE: PRT
<213> ORGANISM: Artificial Sequence
<220> FEATURE:
<223> OTHER INFORMATION: Synthetic pMI

<400> SEQUENCE: 4

Thr Ser Phe Ala Glu Tyr Trp Asn Leu Leu Ser Pro
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic pDIQ

<400> SEQUENCE: 5

Glu Thr Phe Glu His Trp Trp Ser Gln Leu Leu Ser
1               5                   10

<210> SEQ ID NO 6
<211> LENGTH: 73
<212> TYPE: PRT
<213> ORGANISM: Artificial Sequence
<220> FEATURE:
<223> OTHER INFORMATION: Synthetic a3D

<400> SEQUENCE: 6

Met Gly Ser Trp Ala Glu Phe Lys Gln Arg Leu Ala Ala Ile Lys Thr
1               5                   10                  15

Arg Leu Gln Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Ala Leu Arg Lys Glu Ala Ala Ala Ile Arg
    50                  55                  60

Asp Glu Leu Gln Ala Tyr Arg His Asn
65                  70

<210> SEQ ID NO 7
<211> LENGTH: 73
<212> TYPE: PRT
<213> ORGANISM: Artificial Sequence
<220> FEATURE:
<223> OTHER INFORMATION: Synthetic M11

<400> SEQUENCE: 7

Met Gly Ser Trp Ala Glu Phe Ser Gln Arg Leu Phe Ala Ile Tyr Trp
1               5                   10                  15

Arg Leu Leu Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Ala Leu Arg Lys Glu Ala Ala Ala Ile Arg
    50                  55                  60

Asp Glu Leu Gln Ala Tyr Arg His Asn
65                  70

<210> SEQ ID NO 8
<211> LENGTH: 73
<212> TYPE: PRT
<213> ORGANISM: Artificial Sequence
<220> FEATURE:
<223> OTHER INFORMATION: Synthetic M12

<400> SEQUENCE: 8

Met Gly Ser Trp Ala Glu Phe Lys Gln Arg Leu Ala Ala Ile Lys Thr
 1               5                  10                  15

Arg Leu Gln Ala Leu Gly Gly Ser Glu Ala Glu Leu Ala Ala Phe Glu
            20                  25                  30

Lys Glu Ile Phe Ala Phe Tyr Trp Glu Leu Leu Ala Tyr Lys Gly Lys
        35                  40                  45

Gly Asn Pro Glu Val Glu Ala Leu Arg Lys Glu Ala Ala Ala Ile Arg
    50                  55                  60

Asp Glu Leu Gln Ala Tyr Arg His Asn
65                  70

<210> SEQ ID NO 9
<211> LENGTH: 74
<212> TYPE: PRT
<213> ORGANISM: Artificial Sequence
<220> FEATURE:
<223> OTHER INFORMATION: Synthetic M13

<400> SEQUENCE: 9

Met Gly Ser Trp Ala Glu Phe Lys Gln Arg Leu Ala Ala Ile Lys Thr
 1               5                  10                  15

Arg Leu Gln Ala Leu Gly Gly Ser Glu Ala Glu Leu Ala Ala Phe Glu
            20                  25                  30

Lys Glu Ile Ala Ala Phe Glu Ser Glu Leu Gln Ala Tyr Lys Gly Lys
        35                  40                  45

Gly Asn Pro Glu Val Glu Ala Leu Arg Lys Glu Ala Ala Ala Ile Arg
    50                  55                  60

Phe Glu Leu Tyr Trp Tyr Arg Leu Ser Pro
65                  70

<210> SEQ ID NO 10
<211> LENGTH: 73
<212> TYPE: PRT
<213> ORGANISM: Artificial Sequence
<220> FEATURE:
<223> OTHER INFORMATION: Synthetic M14

<400> SEQUENCE: 10

Met Gly Ser Trp Ala Glu Phe Ser Gln Arg Leu Phe Ala Ile Tyr Trp
 1               5                  10                  15

Arg Leu Leu Ala Leu Gly Gly Ser Glu Ala Glu Leu Ala Ala Phe Glu
            20                  25                  30

Lys Glu Ile Phe Ala Phe Tyr Trp Glu Leu Leu Ala Tyr Lys Gly Lys
        35                  40                  45

Gly Asn Pro Glu Val Glu Ala Leu Arg Lys Glu Ala Ala Ala Ile Arg
    50                  55                  60

Asp Glu Leu Gln Ala Tyr Arg His Asn
65                  70

<210> SEQ ID NO 11
<211> LENGTH: 74
<212> TYPE: PRT
<213> ORGANISM: Artificial Sequence

```
<220> FEATURE:
<223> OTHER INFORMATION: Synthetic M15
<400> SEQUENCE: 11

Met Gly Ser Trp Ala Glu Phe Ser Gln Arg Leu Phe Ala Ile Tyr Trp
  1               5                  10                  15

Arg Leu Leu Ala Leu Gly Gly Ser Glu Ala Glu Leu Ala Ala Phe Glu
             20                  25                  30

Lys Glu Ile Ala Ala Phe Glu Ser Glu Leu Gln Ala Tyr Lys Gly Lys
         35                  40                  45

Gly Asn Pro Glu Val Glu Ala Leu Arg Lys Glu Ala Ala Ile Arg
     50                  55                  60

Phe Glu Leu Tyr Trp Tyr Arg Leu Ser Pro
 65                  70

<210> SEQ ID NO 12
<211> LENGTH: 74
<212> TYPE: PRT
<213> ORGANISM: Artificial Sequence
<220> FEATURE:
 <223> OTHER INFORMATION: Synthetic M16

<400> SEQUENCE: 12

Met Gly Ser Trp Ala Glu Phe Lys Gln Arg Leu Ala Ala Ile Lys Thr
  1               5                  10                  15

Arg Leu Gln Ala Leu Gly Gly Ser Glu Ala Glu Leu Ala Ala Phe Glu
             20                  25                  30

Lys Glu Ile Phe Ala Phe Tyr Trp Glu Leu Leu Ala Tyr Lys Gly Lys
         35                  40                  45

Gly Asn Pro Glu Val Glu Ala Leu Arg Lys Glu Ala Ala Ile Arg
     50                  55                  60

Phe Glu Leu Tyr Trp Tyr Arg Leu Ser Pro
 65                  70

<210> SEQ ID NO 13
<211> LENGTH: 74
<212> TYPE: PRT
<213> ORGANISM: Artificial Sequence
<220> FEATURE:
<223> OTHER INFORMATION: Synthetic M17

<400> SEQUENCE: 13

Met Gly Ser Trp Ala Glu Phe Ser Gln Arg Leu Phe Ala Ile Tyr Trp
  1               5                  10                  15

Arg Leu Leu Ala Leu Gly Gly Ser Glu Ala Glu Leu Ala Ala Phe Glu
             20                  25                  30

Lys Glu Ile Phe Ala Phe Tyr Trp Glu Leu Leu Ala Tyr Lys Gly Lys
         35                  40                  45

Gly Asn Pro Glu Val Glu Ala Leu Arg Lys Glu Ala Ala Ile Arg
     50                  55                  60

Phe Glu Leu Tyr Trp Tyr Arg Leu Ser Pro
 65                  70

<210> SEQ ID NO 14
<211> LENGTH: 73
<212> TYPE: PRT
<213> ORGANISM: Artificial Sequence
<220> FEATURE:
<223> OTHER INFORMATION: Synthetic M21

<400> SEQUENCE: 14
```

```
Met Gly Ser Trp Phe Glu Phe Ala Trp Arg Leu Leu Glu Ile Lys Thr
 1               5                  10                  15

Ala Leu Gln Ala Leu Gly Gly Ser Glu Ala Glu Leu Ala Ala Phe Glu
            20                  25                  30

Lys Glu Ile Ala Ala Phe Glu Ser Leu Gln Ala Tyr Lys Gly Lys
        35                  40                  45

Gly Asn Pro Glu Val Glu Ala Leu Arg Lys Glu Ala Ala Ile Arg
    50                  55                  60

Asp Glu Leu Gln Ala Tyr Arg His Asn
65                  70
```

<210> SEQ ID NO 15
<211> LENGTH: 73
<212> TYPE: PRT
<213> ORGANISM: Artificial Sequence
<220> FEATURE:
<223> OTHER INFORMATION: Synthetic M23

<400> SEQUENCE: 15

```
Met Gly Ser Trp Ala Glu Phe Lys Gln Arg Leu Ala Ala Ile Lys Thr
 1               5                  10                  15

Arg Leu Gln Ala Leu Gly Gly Ser Glu Ala Glu Leu Ala Ala Phe Glu
            20                  25                  30

Lys Glu Ile Ala Ala Phe Glu Ser Leu Gln Ala Tyr Lys Gly Lys
        35                  40                  45

Gly Asn Pro Glu Val Glu Ala Leu Arg Phe Glu Ala Tyr Trp Ile Arg
    50                  55                  60

Leu Glu Leu Gln Ala Tyr Arg His Asn
65                  70
```

<210> SEQ ID NO 16
<211> LENGTH: 73
<212> TYPE: PRT
<213> ORGANISM: Artificial Sequence
<220> FEATURE:
<223> OTHER INFORMATION: Synthetic M25

<400> SEQUENCE: 16

```
Met Gly Ser Trp Phe Glu Phe Ala Trp Arg Leu Leu Glu Ile Lys Thr
 1               5                  10                  15

Arg Leu Gln Ala Leu Gly Gly Ser Glu Ala Glu Leu Ala Ala Phe Glu
            20                  25                  30

Lys Glu Ile Ala Ala Phe Glu Ser Leu Gln Ala Tyr Lys Gly Lys
        35                  40                  45

Gly Asn Pro Glu Val Glu Ala Leu Arg Phe Glu Ala Tyr Trp Ile Arg
    50                  55                  60

Leu Glu Leu Gln Ala Tyr Arg His Asn
65                  70
```

<210> SEQ ID NO 17
<211> LENGTH: 30
<212> TYPE: PRT
<213> ORGANISM: Artificial Sequence
<220> FEATURE:
<223> OTHER INFORMATION: Synthetic one alpha-helix of p53LZ2 dimer

<400> SEQUENCE: 17

```
Arg Met Lys Gln Leu Glu Asp Lys Val Gly Glu Leu Leu Phe Ser Asn
 1               5                  10                  15

Tyr Trp Leu Glu Leu Glu Val Ala Arg Leu Lys Lys Leu Val
```

```
<210> SEQ ID NO 18
<211> LENGTH: 9
<212> TYPE: PRT
<213> ORGANISM: Artificial Sequence
<220> FEATURE:
<223> OTHER INFORMATION: Synthetic TAT

<400> SEQUENCE: 18

Arg Lys Lys Arg Arg Gln Arg Arg Arg
1               5

<210> SEQ ID NO 19
<211> LENGTH: 16
<212> TYPE: PRT
<213> ORGANISM: Artificial Sequence
<220> FEATURE:
<223> OTHER INFORMATION: Synthetic MTS (membrane translocating sequence)

<400> SEQUENCE: 19

Ala Ala Val Ala Leu Leu Pro Ala Val Leu Ala Leu Leu Ala Pro
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: Synthetic MTS fragment

<400> SEQUENCE: 20

Ala Ala Val Ala Leu Leu Pro
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic MTS fragment

<400> SEQUENCE: 21

Ala Val Leu Leu Ala Leu Leu Ala Pro
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic NLS (nuclear localization sequence)

<400> SEQUENCE: 22

Lys Lys Lys Arg Lys
1               5

<210> SEQ ID NO 23
<211> LENGTH: 4
<212> TYPE: PRT
<213> ORGANISM: Artificial Sequence
<220> FEATURE:
<223> OTHER INFORMATION: Synthetic NLS (nuclear localization sequence)

<400> SEQUENCE: 23

Lys Lys Lys Arg
1
```

-continued

```
<210> SEQ ID NO 24
<211> LENGTH: 6
<212> TYPE: PRT
<213> ORGANISM: Artificial Sequence
<220> FEATURE:
<223> OTHER INFORMATION: Synthetic NLS (nuclear localization sequence)

<400> SEQUENCE: 24

Lys Lys Lys Arg Lys Arg
  1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic NLS (nuclear localization sequence)

<400> SEQUENCE: 25

Arg Arg Arg Arg Arg
  1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic NLS (nuclear localization sequence)

<400> SEQUENCE: 26

Arg Arg Arg Arg Arg Arg
  1               5

<210> SEQ ID NO 27
<211> LENGTH: 21
<212> TYPE: PRT
<213> ORGANISM: Artificial Sequence
<220> FEATURE:
<223> OTHER INFORMATION: Synthetic Fusion peptide of MTS and NLS

<400> SEQUENCE: 27

Ala Ala Val Ala Leu Leu Pro Ala Val Leu Leu Ala Leu Leu Ala Pro
  1               5                  10                  15

Lys Lys Lys Arg Lys
             20

<210> SEQ ID NO 28
<211> LENGTH: 74
<212> TYPE: PRT
<213> ORGANISM: Artificial Sequence
<220> FEATURE:
<223> OTHER INFORMATION: Synthetic Modified three-helix bundle protein
<220> FEATURE:
<221> NAME/KEY: MOD_RES
<222> LOCATION: (5)
<223> OTHER INFORMATION: Xaa is A or F
<220> FEATURE:
<221> NAME/KEY: MOD_RES
<222> LOCATION: (8)
<223> OTHER INFORMATION: Xaa is K, S, or A
<220> FEATURE:
<221> NAME/KEY: MOD_RES
<222> LOCATION: (9)
<223> OTHER INFORMATION: Xaa is Q or W
<220> FEATURE:
<221> NAME/KEY: MOD_RES
<222> LOCATION: (12)
<223> OTHER INFORMATION: Xaa is A, F, or L
```

```
<220> FEATURE:
<221> NAME/KEY: MOD_RES
<222> LOCATION: (13)
<223> OTHER INFORMATION: Xaa is A or E
<220> FEATURE:
<221> NAME/KEY: MOD_RES
<222> LOCATION: (15)
<223> OTHER INFORMATION: Xaa is K or Y
<220> FEATURE:
<221> NAME/KEY: MOD_RES
<222> LOCATION: (16)
<223> OTHER INFORMATION: Xaa is T or W
<220> FEATURE:
<221> NAME/KEY: MOD_RES
<222> LOCATION: (19)
<223> OTHER INFORMATION: Xaa is Q or L
<220> FEATURE:
<221> NAME/KEY: MOD_RES
<222> LOCATION: (36)
<223> OTHER INFORMATION: Xaa is A or F
<220> FEATURE:
<221> NAME/KEY: MOD_RES
<222> LOCATION: (39)
<223> OTHER INFORMATION: Xaa is E or Y
<220> FEATURE:
<221> NAME/KEY: MOD_RES
<222> LOCATION: (40)
<223> OTHER INFORMATION: Xaa is S or W
<220> FEATURE:
<221> NAME/KEY: MOD_RES
<222> LOCATION: (43)
<223> OTHER INFORMATION: Xaa is is Q or L
<220> FEATURE:
<221> NAME/KEY: MOD_RES
<222> LOCATION: (58)
<223> OTHER INFORMATION: Xaa is K or F
<220> FEATURE:
<221> NAME/KEY: MOD_RES
<222> LOCATION: (61)
<223> OTHER INFORMATION: Xaa is A or Y
<220> FEATURE:
<221> NAME/KEY: MOD_RES
<222> LOCATION: (62)
<223> OTHER INFORMATION: Xaa is A or W
<220> FEATURE:
<221> NAME/KEY: MOD_RES
<222> LOCATION: (65)
<223> OTHER INFORMATION: Xaa is D, F, or L
<220> FEATURE:
<221> NAME/KEY: MOD_RES
<222> LOCATION: (68)
<223> OTHER INFORMATION: Xaa is Q or Y
<220> FEATURE:
<221> NAME/KEY: MOD_RES
<222> LOCATION: (69)
<223> OTHER INFORMATION: Xaa is A or W
<220> FEATURE:
<221> NAME/KEY: MOD_RES
<222> LOCATION: (72)
<223> OTHER INFORMATION: Xaa is H or L
<220> FEATURE:
<221> NAME/KEY: MOD_RES
<222> LOCATION: (73)
<223> OTHER INFORMATION: Xaa is N or S
<220> FEATURE:
<221> NAME/KEY: MOD_RES
<222> LOCATION: (74)
<223> OTHER INFORMATION: Xaa is absent or P

<400> SEQUENCE: 28

Met Gly Ser Trp Xaa Glu Phe Xaa Xaa Arg Leu Xaa Xaa Ile Xaa Xaa
 1               5                  10                  15

Arg Leu Xaa Ala Leu Gly Gly Ser Glu Ala Glu Leu Ala Ala Phe Glu
            20                  25                  30

Lys Glu Ile Xaa Ala Phe Xaa Xaa Glu Leu Xaa Ala Tyr Lys Gly Lys
        35                  40                  45
```

```
Gly Asn Pro Glu Val Glu Ala Leu Arg Xaa Glu Ala Xaa Xaa Ile Arg
    50                  55                  60

Xaa Glu Leu Xaa Xaa Tyr Arg Xaa Xaa Xaa
65                  70
```